US012773573B2

(12) United States Patent
Boskovitz et al.

(10) Patent No.: US 12,773,573 B2
(45) Date of Patent: Oct. 27, 2026

(54) SYSTEM AND METHOD FOR DETERMINING HUMAN SKIN ATTRIBUTES AND TREATMENTS

(71) Applicant: LUMENIS BE LTD., Yokneam (IL)

(72) Inventors: Victor Boskovitz, Yokneam (IL); Andrey Gandman, Yokneam (IL)

(73) Assignee: LUMENIS BE LTD., Yokneam (IL)

( * ) Notice: Subject to any disclaimer, the term of this patent is extended or adjusted under 35 U.S.C. 154(b) by 323 days.

(21) Appl. No.: 18/518,708

(22) Filed: Nov. 24, 2023

(65) Prior Publication Data

US 2024/0173562 A1 May 30, 2024

Related U.S. Application Data

(60) Provisional application No. 63/428,827, filed on Nov. 30, 2022, provisional application No. 63/428,832, (Continued)

(51) Int. Cl.

*A61N 5/06* (2006.01)
*A61B 5/00* (2006.01)
*A61N 5/067* (2006.01)

(52) U.S. Cl.

CPC .......... *A61N 5/0616* (2013.01); *A61B 5/0077* (2013.01); *A61B 5/444* (2013.01); (Continued)

(58) Field of Classification Search

CPC .... A61N 5/0616; A61N 5/067; A61B 5/0077; A61B 5/444; A61B 5/7267; A61B 5/742; A61B 5/443

See application file for complete search history.

(56) References Cited

U.S. PATENT DOCUMENTS 11,278,236 B2 * 3/2022 Patwardhan ......... A61B 5/0082
2006/0227137 A1 10/2006 Weyrich et al.
(Continued)

FOREIGN PATENT DOCUMENTS

EP 3933680 1/2022
EP 3933680 A1 * 1/2022 ............ B26B 19/38
(Continued)

OTHER PUBLICATIONS

McMullen R. et al. "Imaging Techniques and Analysis for Quantification of Skin Appearance". Plastic Surgery Key. Internet Archive. Oct. 27, 2016. https://web.archive.org/web/20161027182136/https://plasticsurgerykey.com/imaging-techniques-and-analysis-for-quantification-of-skin-appearance/ (Year: 2016).*
(Continued)

*Primary Examiner* — Unsu Jung
*Assistant Examiner* — Emily N Cirulnick
(74) *Attorney, Agent, or Firm* — ISUS Intellectual Property PLLC; Anthony Jason Mirabito

(57) ABSTRACT

The present disclosure relates to a method and system for automatically determining and generating human skin attributes and attribute maps by a skin diagnostic and aesthetic treatment system. The present disclosure proposes to automate the process of determining various skin attributes by using one or more trained models using the determined skin attributes to identify treatment parameter for an energy-based treatment system.

21 Claims, 23 Drawing Sheets

Flow chart for LUT models

Related U.S. Application Data filed on Nov. 30, 2022, provisional application No. 63/428,835, filed on Nov. 30, 2022, provisional application No. 63/428,877, filed on Nov. 30, 2022, provisional application No. 63/428,892, filed on Nov. 30, 2022, provisional application No. 63/428,849, filed on Nov. 30, 2022.

(52) U.S. Cl.
CPC ............ *A61B 5/7267* (2013.01); *A61B 5/742* (2013.01); *A61N 5/067* (2021.08)

(56) References Cited

U.S. PATENT DOCUMENTS

| | | | | |
|---|---|---|---|---|
| 2010/0249731 | A1 | 9/2010 | Stamatas et al. | |
| 2016/0228048 | A1* | 8/2016 | Sun | A61B 5/443 |
| 2017/0294015 | A1* | 10/2017 | Wang | G06T 7/0012 |
| 2019/0366119 | A1* | 12/2019 | Kim | G06T 7/0012 |
| 2020/0297267 | A1 | 9/2020 | Wei | |
| 2021/0209754 | A1* | 7/2021 | Mishra | G06T 7/90 |
| 2021/0220667 | A1* | 7/2021 | Schuster | A61N 5/0616 |
| 2021/0406589 | A1* | 12/2021 | Yadav | G06T 7/11 |
| 2022/0203115 | A1 | 6/2022 | Gandman et al. | |

FOREIGN PATENT DOCUMENTS

| | | | | |
|---|---|---|---|---|
| IL | 296542 | | 11/2022 | |
| WO | WO-2018049215 | A1 * | 2/2018 | A61B 1/00186 |
| WO | WO-2021186443 | A1 * | 9/2021 | G06N 3/045 |
| WO | WO-2022126277 | A1 * | 6/2022 | G01N 21/31 |
| WO | 2022174091 | | 8/2022 | |
| WO | WO-2022174091 | A1 * | 8/2022 | A61M 1/00 |

OTHER PUBLICATIONS

Shrestha R. et al. Multispectral imaging using LED illumination and an RGB camera. 21st Color and Imaging Conference Final Program and Proceedings. 2013; p. 8-13. (Year: 2013).*

Bernstein et al. Chapter 14 Laser and Energy-Based Devices for the Consumer: The Future of Esthetic Energy-Based Devices. Laser and Light Source Treatments for the Skin. 2014; p. 186-192. (Year: 2014).*

Langeveld M, et al. Skin measurement devices to assess skin quality: A systematic review on reliability and validity. Skin Res Technol. Mar. 2022;28(2):212-224. doi: 10.1111/srt.13113. (Year: 2022).*

Ward WH, et al. Clinical Presentation and Staging of Melanoma. Cutaneous Melanoma: Etiology and Therapy [Internet]. Dec. 21, 2017. Table 1, Fitzpatrick Classification of Skin Types I through VI. doi: 10.15586/codon.cutaneousmelanoma.2017.ch6 (Year: 2022).*

BLT Inc. “What is a lookup table (LUT)?” Aug. 20, 2025 https://bltinc.com/2025/08/20/what-is-a-lookup-table-lut/ (Year: 2025).*

Search Report—corresponding PCT Application No. PCT/IB23/61878, dated Mar. 28, 2024, 3 pages.

* cited by examiner

| W450 | W490 | W570 | W590 | W660 | W730 | W850 | Mel | ERY | Scat |
|---|---|---|---|---|---|---|---|---|---|
| 0.015491 | 0.036868 | 0.059944 | 0.065692 | 0.3076 | 0.42186 | 0.48274 | 0.11 | 0.05 | 0.55 |
| 0.015748 | 0.037417 | 0.061246 | 0.067113 | 0.30886 | 0.42382 | 0.48615 | 0.11 | 0.05 | 0.57 |
| 0.015999 | 0.037951 | 0.062522 | 0.068507 | 0.31006 | 0.42568 | 0.48938 | 0.11 | 0.05 | 0.59 |
| 0.016246 | 0.03847 | 0.063773 | 0.069875 | 0.31123 | 0.42745 | 0.49246 | 0.11 | 0.05 | 0.61 |
| 0.016487 | 0.038977 | 0.065001 | 0.071217 | 0.31236 | 0.42914 | 0.49538 | 0.11 | 0.05 | 0.63 |
| 0.019421 | 0.044898 | 0.080035 | 0.087663 | 0.32535 | 0.44726 | 0.52588 | 0.11 | 0.05 | 0.91 |
| 0.019603 | 0.045254 | 0.080977 | 0.088693 | 0.32613 | 0.44829 | 0.52755 | 0.11 | 0.05 | 0.93 |
| 0.019783 | 0.045601 | 0.081904 | 0.089708 | 0.3269 | 0.44929 | 0.52916 | 0.11 | 0.05 | 0.95 |
| 0.01996 | 0.045942 | 0.082816 | 0.090706 | 0.32765 | 0.45027 | 0.53073 | 0.11 | 0.05 | 0.97 |
| 0.020134 | 0.046275 | 0.083713 | 0.091688 | 0.32839 | 0.45123 | 0.53226 | 0.11 | 0.05 | 0.99 |
| 0.027571 | 0.047272 | 0.10932 | 0.11736 | 0.16102 | 0.18296 | 0.17162 | 0.112 | 0.001 | 0.05 |
| 0.030484 | 0.05318 | 0.128 | 0.13803 | 0.19258 | 0.22533 | 0.21959 | 0.112 | 0.001 | 0.07 |
| 0.032346 | 0.057008 | 0.14111 | 0.15268 | 0.21576 | 0.25816 | 0.25911 | 0.112 | 0.001 | 0.09 |
| 0.037661 | 0.067354 | 0.17956 | 0.19626 | 0.28909 | 0.3762 | 0.42464 | 0.112 | 0.001 | 0.25 |
| 0.038011 | 0.067952 | 0.18156 | 0.19852 | 0.29285 | 0.38303 | 0.43578 | 0.112 | 0.001 | 0.27 |
| 0.03834 | 0.068507 | 0.18334 | 0.20053 | 0.29615 | 0.38907 | 0.44582 | 0.112 | 0.001 | 0.29 |
| 0.038652 | 0.069028 | 0.18496 | 0.20234 | 0.29908 | 0.39444 | 0.4549 | 0.112 | 0.001 | 0.31 |
| 0.039506 | 0.07044 | 0.1891 | 0.20695 | 0.3062 | 0.40754 | 0.47764 | 0.112 | 0.001 | 0.37 |
| 0.039768 | 0.070871 | 0.19031 | 0.20828 | 0.30816 | 0.41113 | 0.48401 | 0.112 | 0.001 | 0.39 |
| 0.040021 | 0.071287 | 0.19145 | 0.20954 | 0.30998 | 0.41443 | 0.4899 | 0.112 | 0.001 | 0.41 |

FIG. 9

| | B | | G | | R | | | |
|---|---|---|---|---|---|---|---|---|
| | **W450** | **W490** | **W570** | **W590** | **W660** | **W850** | **Mel** | **Ery** |
| | 0.277256 | 0.282264 | 0.26329 | 0.25823 | 0.472806 | 0.509204 | 0.06 | 0.11 |
| | 0.275928 | 0.27901 | 0.25961 | 0.252157 | 0.469128 | 0.503964 | 0.06 | 0.12 |
| | 0.274746 | 0.27611 | 0.25637 | 0.246803 | 0.46553 | 0.49884 | 0.06 | 0.13 |
| | 0.273689 | 0.273507 | 0.253493 | 0.242058 | 0.462008 | 0.493829 | 0.06 | 0.14 |
| | 0.272738 | 0.271157 | 0.250919 | 0.237832 | 0.458559 | 0.488925 | 0.06 | 0.15 |
| | 0.271878 | 0.269022 | 0.248599 | 0.23405 | 0.45518 | 0.484125 | 0.06 | 0.16 |
| | 0.271097 | 0.267071 | 0.246494 | 0.230649 | 0.451868 | 0.479424 | 0.06 | 0.17 |
| | 0.270386 | 0.265281 | 0.244572 | 0.227578 | 0.448621 | 0.474819 | 0.06 | 0.18 |
| | 0.269734 | 0.263628 | 0.242806 | 0.224793 | 0.445437 | 0.470307 | 0.06 | 0.19 |
| | 0.269136 | 0.262097 | 0.241175 | 0.222255 | 0.442312 | 0.465884 | 0.06 | 0.2 |
| 1205 | 0.344597 | 0.3706 | 0.387709 | 0.44402 | 0.507383 | 0.56948 | 0.065 | 0.002 |
| | 0.336146 | 0.365958 | 0.380395 | 0.434344 | 0.506398 | 0.56802 | 0.065 | 0.004 |
| | 0.329428 | 0.36166 | 0.373725 | 0.425427 | 0.505421 | 0.566576 | 0.065 | 0.006 |
| | 0.323931 | 0.357647 | 0.367576 | 0.417131 | 0.504452 | 0.565147 | 0.065 | 0.008 |
| | 0.319346 | 0.35388 | 0.361867 | 0.409362 | 0.503491 | 0.563732 | 0.065 | 0.01 |
| | 0.315465 | 0.350327 | 0.356539 | 0.402054 | 0.502538 | 0.562329 | 0.065 | 0.012 |
| | 0.31214 | 0.346967 | 0.351547 | 0.395154 | 0.501592 | 0.56094 | 0.065 | 0.014 |
| | 0.30926 | 0.34378 | 0.346855 | 0.388622 | 0.500653 | 0.559562 | 0.065 | 0.016 |
| 1203 | 0.306742 | 0.340751 | 0.342435 | 0.382424 | 0.499722 | 0.558196 | 0.065 | 0.018 |

FIG. 12

Flow chart for LUT models

Flow chart for RGB maps based on LUT

Flow chart Depth Lesions Map

SYSTEM AND METHOD FOR DETERMINING HUMAN SKIN ATTRIBUTES AND TREATMENTS

RELATED APPLICATIONS

This application is a continuation to U.S. Provisional Application No. 63/428,827 filed Nov. 30, 2022, entitled "System and Method for Skin Type Determination", U.S. Provisional Application No. 63/428,832 filed Nov. 30, 2022, entitled "System and Method for Determining Human Skin Attributes", U.S. Provisional Application No. 63/428,835 fled Nov. 30, 2022, entitled "System and Method for Masking Hair in a Skin Diagnostic System", U.S. Provisional Application No. 63/428,849 fled Nov. 30, 2022, entitled "System and Method for Identifying Vascular Structure Depth in Skin", U.S. Provisional Application No. 63/428,877 flied Nov. 30, 2022, entitled "System and Method for Determining Pigment Intensity in a Diagnostic System", and U.S. Provisional Application No. 63/428,892 filed Nov. 30, 2022, entitled "System and Method for Identifying Pigment Structure Depth in skin", the entire contents of these applications are herein incorporated by reference.

BACKGROUND

Therapeutic and aesthetic energy-based treatments are utilized for therapeutic and aesthetic treatments on target skin. Typically, medical personnel diagnose various skin conditions and set parameters of a machine that delivers an energy-based treatment. An energy-based treatment may be one that targets tissue of the target skin, gets absorbed by one or more chromophores and causes a cascade of reactions, including photochemical, photothermal, thermal, photoacoustic, acoustic, healing, ablation, coagulation, biological, tightening, or other any other physiological effect. Those reactions create the desired treatment outcomes such as permanent hair removal, hair growth, pigmented or vascular lesion treatment of soft tissue, rejuvenation or tightening, acne treatment, cellulite treatment, vein collapse, or tattoo removal which may include mechanical breakdown of tattoo pigments and crusting.

Therapeutic and aesthetic treatments focus on altering aesthetic appearance through the treatment of conditions including scars, skin laxity, wrinkles, moles, liver spots, excess fat, cellulite, unwanted hair, skin discoloration, spider veins and so on. Target skin is subjected to the treatment using energy-based system, such as laser and/or light energy-based systems. In these treatments, light energy with pre-defined parameters may be typically projected on the target skin area. Medical personnel may have to consider skin attributes such as skin type, presence of tanning, hair color, hair density, hair thickness, blood vessel diameter and depth, lesion type, pigment depth, pigment intensity, tattoo color and type, in order to decide treatment parameters to be used.

SUMMARY OF DESCRIBED SUBJECT MATTER

In one aspect of the current disclosure, a system for determining skin attributes and treatment parameters of target skin for an aesthetic skin diagnosis and treatment unit, comprises: a display; at least one source for illumination light; an image capture device; a source for providing energy-based treatment; a processor. Also, a memory communicatively coupled to the processor, wherein the memory stores processor-executable instructions, which, on execution, cause the processor to: activate the at least one source for illumination light to illuminate in a plurality of monochromatic wavelengths; obtain images from the image capture device in the plurality of monochromatic wavelengths; receive target skin data comprising data of each pixel of the obtained images; analyze the target skin data using a plurality of trained skin attribute models; determine, with the trained skin attribute models, at least one sin attributes classification of the target skin; analyze, with a trained skin treatment model, the at least one classification for the skin attributes of the target skin; identify, with the trained skin treatment model, treatment parameters for the source of energy-based treatment for the at least one skin attributes classification determined; and display the treatment parameters identified to treat the skin attributes.

In one aspect of the current disclosure, the system generates and displays a list of attributes of the target skin based on the analysis by the trained akin attribute models. The source of energy-based treatment is activated to treat the target skin with the treatment parameters determined. Also the plurality of trained skin attribute models are trained by; (i) providing a plurality of labelled images of at least one skin attribute stored in a database to the akin attribute models, and (ii) configuring the skin attribute models to classify the plurality of labelled images into at least one skin attribute.

In another aspect of the current disclosure the plurality of different wavelengths comprises 450 nm, 490 nm, 570 nm, 590 nm, 660 nm, 770 nm, and 850 nm. The processor is further configured, after obtaining the images, to register and align the images of the plurality of monochromatic wavelengths and to generate and display a map of the target skin with any combination of the plurality of monochromatic wavelengths or configured to generate and display a map of the target skin from the wavelengths that represent red, green, and blue.

In yet another aspect of the current disclosure one of the skin attributes is hair on the target skin and a hair mask model is one of the plurality of skin attribute models and the processor is further configured to: receive the target skin data of one monochromatic wavelengths of the plurality of monochromatic wavelengths; and determine, with the hair mask model, one of two classifications, hair or background, for each pixel of an image of the one monochromatic wavelength.

In a further aspect of the current disclosure the processor is further configured to: instruct additional skin attribute models to remove hair pixels labeled hair by the hair mask model from further analysis of target skin. One of the skin attributes is skin type and a skin type model is one of the plurality of skin attribute models. The processor is further configured to: receive skin type data comprising an average calibrated reflectance value of total pixels of each monochrome image; and determine, with the skin type model, six classifications of skin type. The skin attribute is at least one of: melanin density, vascular density or scattering.

In some aspects of the current disclosure the processor is further configured to: receive skin type data comprising a plurality of absolute reflectance values for each pixel representing the plurality of wavelengths; analyze the plurality of absolute values per pixel, with at least one of a melanin model or a vascular model, compared with a look up table (LUT) values, wherein the LUT comprises values for skin models that represent known physical models of illumination effects on human skin and represent physical measurements of concentration of the skin attributes in the target skin; and identify for each pixel the one LUT entry for at least one of melanin density or vascular density with the value closest in distance to the plurality of measured absolute values for each pixel, wherein this distance may be a similarity of certain distances.

In yet another aspect of the current disclosure one of the skin attributes is vascular lesion depth and a vascular depth model is one of the plurality of skin attribute models. The processor is further configured to: receive the target skin data of the plurality of monochromatic wavelengths; and determine a classification for each pixel, with the vascular lesion model, of one of four classifications, deep vascular, medium vascular, shallow vascular or background; and generate and display a map with markings to illustrate the classifications of vascular lesion depths.

In a further aspect of the current disclosure one of the skin attributes is pigment lesion depth and a pigment depth model is one of the plurality of skin attribute models. The processor is further configured to: receive the target skin data of two monochromatic of the plurality of monochromatic wavelengths, wherein one monochromatic wavelength represents the lowest wavelength value of the system, and the second monochromatic wavelength represents the highest wavelength value of the system; receive, from the vascular depth model, classified pixels of vascular depth; analyze the pixels not classified by the vascular depth model, for outliers in darkness for each of the two monochromatic wavelengths; determine a classification for each pixel analyzed, with the pigment lesion model, the outliers of the lowest wavelength value as shallow pigment lesions and the highest wavelength value as deep pigment lesions; and generate and display a map with markings to illustrate the classifications of pigment lesion depths.

In another aspect of the current disclosure one of the skin attributes is pigment lesion intensity and a pigment intensity model is one of the plurality of skin attribute models. The processor is further configured to: receive the target skin data of three features from each of the plurality of monochromatic images, wherein the features are a threshold of a 99-percentile of concentration of melanin representing the lesion, and a calculated median melanin level of the whole image, from a melanin density model and the 99-percentile subtracted from the calculated median melanin level; and determine, based on the features, if the pigment lesion intensity is either a light or dark lesion.

In one aspect of the current disclosure the processor is further configured to: receive the value in the LUT of at least one of, the melanin density value from the melanin model or the vascular density value from the vascular model; compute a new value for the melanin density value or the vascular density value based on setting other skin attributes on the LUT closest to zero; and generate a map of either the melanin density or the vascular density using the new value wavelengths computed.

In an additional aspect of the current disclosure the processor with the trained skin treatment model, are further configured to receive information of; treatment safety parameters, energy treatment source capability parameters, at least one skin area to treat from a user, at least one skin problem indication for treatment based on the skin area to treat from a user, output of the plurality of the skin attribute models related to the at least one skin problem indication. Then the processor and the trained skin treatment model determine, based on the information received, target skin treatment parameters of the energy-based treatment; and display the target skin treatment parameters of the energy-based treatment.

Wherein the determination of the akin treatment parameters is done with a treatment look up table and the processor is further configured to: determine which one of a plurality of skin treatment look up tables, each of the skin treatment look up tables is based on a particular skin problem indication; match the output of the plurality of the skin attribute models to a treatment parameter of the determined skin treatment look up table; and display the matched skin treatment parameters of the energy-based treatment.

Also wherein the processor with the trained skin treatment model, are further configured to: generate and display a red green and blue (RGB) image of the target skin; generate and save to memory at least one of a plurality of maps, display the at least one generated map, wherein the at least one of the plurality of maps comprises; melanin density map, vascular density map, pigment lesion depth map, vascular lesion depth map, pigment intensity, or any combination thereof. The at least one skin problem indication is at least one of; pigment lesions, vascular lesions, combination pigment and vascular lesion, hair removal, or any combination thereof.

In an additional aspect of the current disclosure there is a method for determining skin attributes and treatment parameters of target skin comprises: providing a display, at least one source for illumination light, an image capture device, a source for providing energy-based treatment, a memory and processor, activating, by the processor, the at least one source for illumination light to illuminate in a plurality of monochromatic wavelengths; obtaining, by the processor, images from the image capture device in the plurality of monochromatic wavelengths; receiving, by the processor, target skin data comprising data of each pixel of the obtained Images; analyzing, by the processor, the target skin data using a plurality of trained skin attribute models; determining, by the processor with the trained skin attribute models, at least one skin attributes classification of the target skin; analyzing, by the processor with a trained skin treatment model, the at least one classification for the skin attributes of the target skin; identibring, by the processor with the trained skin treatment model, treatment parameters for the source of energy-based treatment for the at least one skin attributes classification determined; and displaying, by the processor, the treatment parameters identified to treat the skin attributes.

The method may further include the skin attribute is at least one of; melanin density, vascular density and scattering, and wherein the method further comprises: receiving, by the processor, skin type data comprising a plurality of absolute reflectance values for each pixel representing the plurality of wavelengths; analyzing, by the processor, the plurality of absolute values per pixel, with at least one of a melanin model or a vascular model, compared with a look up table (LUT) values, wherein the LUT comprises values for skin models that represent known physical models of illumination effects on human skin and represent physical measurements of concentration of the skin attributes in the target skin; and identifying, by the processor, for each pixel the one LUT entry for at least one of melanin density or vascular density with the value closest in distance to the plurality of measured absolute values for each pixel, wherein this distance may be a similarity of certain distances.

A map generation method wherein the method further comprises: receiving, by the processor, the value in the LUT of at least one of, the melanin density value from the melanin model or the vascular density value from the vascular model; computing, by the processor, a new value for the melanin density value or the vascular density value based on setting other skin attributes on the LUT closest to zero; and generating, by the processor, a map of either the melanin density or the vascular density using the new value wavelengths computed.

In yet another aspect of the current disclosure the method further comprises: receiving, by the processor with the trained skin treatment model information of; treatment safety parameters, energy treatment source capability parameters, at least one skin area to treat from a user, at least one skin problem indication for treatment based on the skin area to treat from a user, and output of the plurality of the skin attribute models related to the at least one skin problem indication. Then determining, by the processor with the trained skin treatment model, based on the information received, target skin treatment parameters of the energy-based treatment; and displaying, by the processor with the trained skin treatment model, the target skin treatment parameters of the energy-based treatment.

In a final aspect of the current disclosure the determining of the skin treatment parameters is done with a treatment look up table and the method further comprise: determining, by the processor with the trained skin treatment model, which one of a plurality of skin treatment look up tables, wherein each of the skin treatment look up tables is based on a particular skin problem indication; matching, by the processor with the trained skin treatment model, the output of the plurality of the skin attribute models to a treatment parameter of the determined skin treatment look up table; and displaying, by the processor, the matched skin treatment parameters of the energy-based treatment.

BRIEF DESCRIPTION OF THE DRAWINGS

Various embodiments of the present disclosure can be further explained with reference to the attached drawings, wherein like structures are referred to by like numerals throughout the several views. The drawings shown are not necessarily to scale, with emphasis instead generally being placed upon illustrating the principles of the present disclosure. Therefore, specific structural and functional details disclosed herein are not to be interpreted as limiting, but merely as a representative basis for teaching one skilled in the art one or more illustrative embodiments.

FIG. 9 is an example of a look up table as used by the current invention.

FIG. 12 is a second example of a look up table as used by the current invention.

DETAILED DESCRIPTION

Figure 1A:
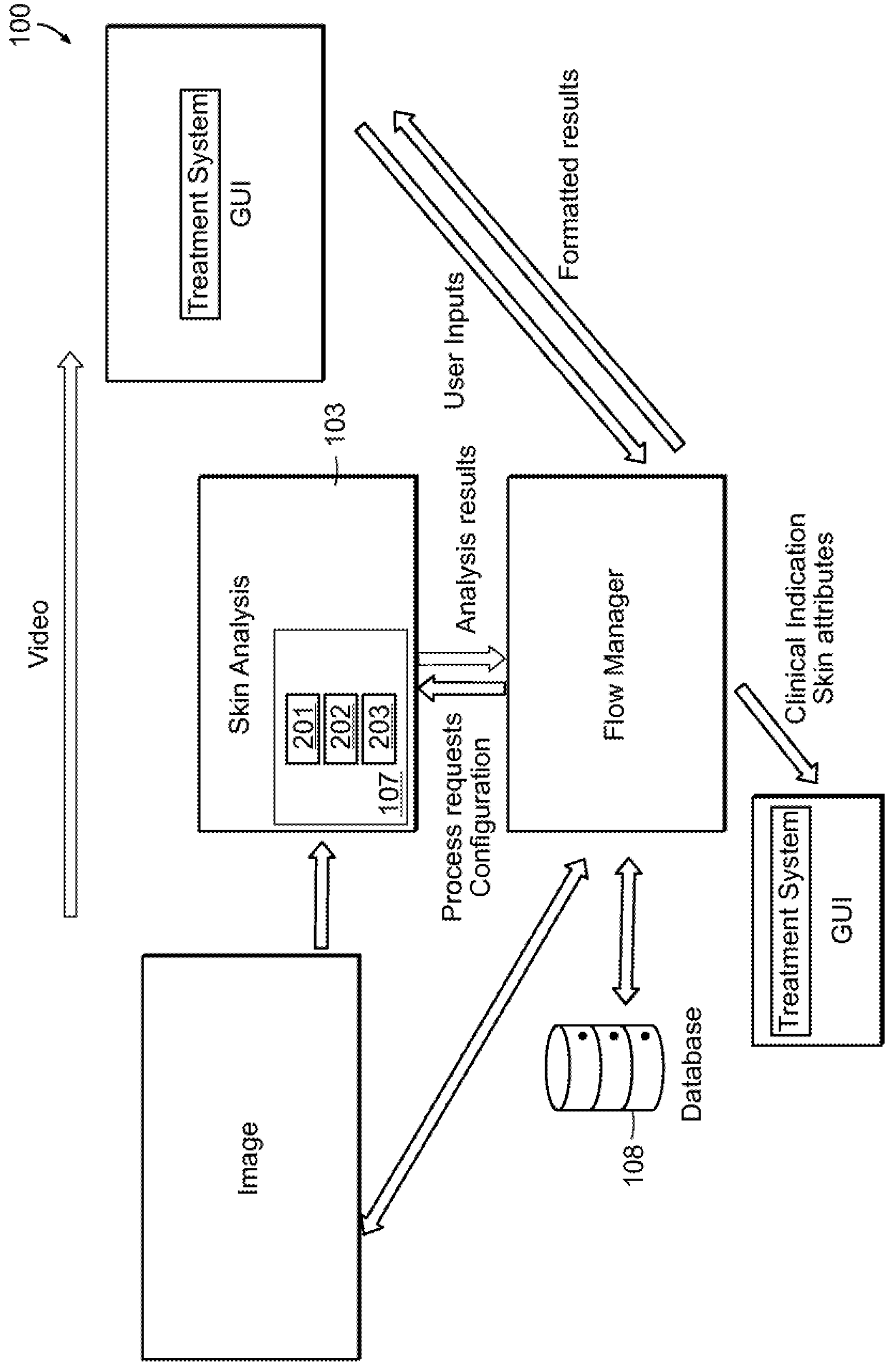
FIGS. 1A and 1B is a block diagram of a skin diagnostic system of the current invention.

Various detailed embodiments of the present disclosure, taken in conjunction with the accompanying figures, are disclosed herein; however, it is to be understood that the disclosed embodiments are merely illustrative. In addition, each of the examples given in connection with the various embodiments of the present disclosure is intended to be illustrative, and not restrictive.

Skin tissue is a very complex biological organ. Although the basic structure is common to all humans, there are many variations within the different areas in a specific individual and among individuals. Variations include skin color (melanin content in Basal layer), hair color and thickness, collagen integrity, blood vessel structure, vascular and pigmented lesions of various types, foreign objects like tattoos, etc.

Various embodiments of the present disclosure provide a technical solution by using a target skin diagnostic system that may be included in a skin treatment system to assist medical personnel to select optimal treatment presets and determine target skin attributes associated with skin conditions, skin diseases or skin reactions to treatment. In some embodiments, data of an area of skin, target skin, will be collected before and after treatment, and this data may be compared for immediate analysis of how to continue to treat the target skin. In some embodiments, target skin responses to treatment are further used to determine the efficacy of treatment and to train a treatment module, as a specific example, humidity present in the skin after treatment is determined.

The present disclosure relates to method and system for determining a plurality of attributes, features, and characteristic (hereinafter skin attributes) of target skin of a person by a skin diagnostic system that may be part of aesthetic skin treatment system. The present disclosure proposes to automate the process of determining the plurality of skin attributes by type by using one or more trained models.

The one or more trained models are trained with a huge set of parameters related to the classification of the plurality skin attributes of the target skin, to output specific skin attributes of the target skin of a person. Among the skin attributes may include, but not limited to; skin type using the Fitzpatrick scale, pigment, or melanin (hereinafter melanin), vascular or erythema (hereinafter vascular), pigment lesion intensity, pigment lesion depth, vascular lesion depth, masking hair data, and a scattering coefficient of the skin. The scattering coefficient is a measure of the ability of particles to scatter photons out of a beam of light.

In some embodiments, skin attributes may be determined for tattoo removal. In tattoo removal, the challenges are twofold. First, to destroy tattoo ink selectively, the best energy-based method such as a laser wavelength should be chosen to achieve selective absorption for the particular ink color or colors while minimizing non-specific effects. However, commonly used tattoo inks are very little regulated, and this ink composition is highly variable. As a result, what appear to be similar ink colors may have wide peak absorption range and the medical personnel has no way to determine the exact type/properties of the specific ink and thus the optimal treatment to be used. Moreover, in addition to the ink's color properties, the skin type (amount of melanin), the depth of the ink and the amount should also be considered for optimal energy based setting and clinical outcomes. Second, in addition to the ink's color properties, the skin type (amount of melanin), the depth of the ink and the amount should also be considered for optimal parameters and clinical outcomes.

Further, Principal Component Analysis (PCA) may be used which enable robust classification of valuable parameters while reducing overall dimensionality of the acquired data. In other words, PCA differentiates data features with respect to their importance to the final clinical outcome. The most relevant parameters may be employed for the development of a physical energy-based treatment interaction model, including, for example, thermal relaxation and soft tissue coagulation. Moreover, large amounts of highly correlated data allow for construction of empirical equations which are based on quantitative immediate biological responses like erythema in hair removal and frosting formation in tattoo removal treatments. Currently, immediate responses are subjectively assessed in a non-quantitative manner by medical personnel without any dynamical quantification. Details on use of PCA and of methods/system for tattoo removal is further described in U.S. application Ser. No. 17/226,235 filed 9 Apr. 2021 which is hereby incorporated by reference in its entirety.

Values and/or maps are generated by the skin diagnostic system for skin attributes, such as but not limited to; density of melanin, density of vascular, map of pigment depth, a map of vascular depth, and a map of optical properties and these properties may or may not reveal physical conditions of the target skin.

FIG. 1A illustrates an example block diagram of a skin diagnostic system 100 that may be integrated in an energy-based treatment system. Energy based treatments may include but are not limited to lasers, intense pulsed light, radio frequency, ultrasound, visible light, ultra-violet light, light-emitting diodes (LED), or any combination thereof. Skin analysis module 103, in accordance with some embodiments of the present disclosure, may include one or more modules 107 that may be in the memory of the skin diagnostic system. It will be appreciated that such modules may be represented as a single module or a combination of different modules. It will be appreciated that such modules may be represented as a single treatment module or a combination of different treatment modules.

Figure 1B:
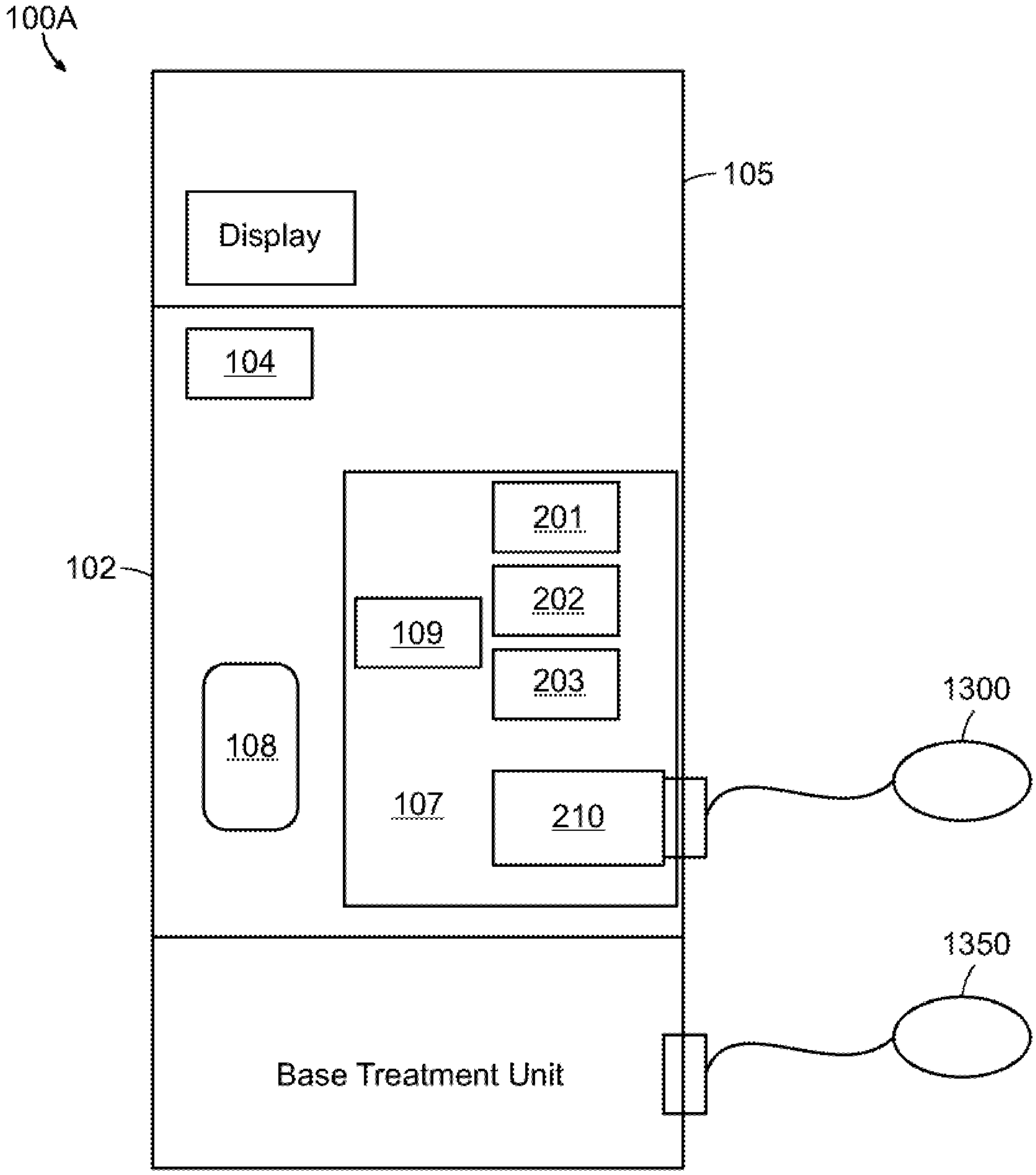

FIG. 1B also illustrates an example of the block diagram wherein the skin diagnostic system 100A includes processor or controller 104, hereinafter processor. Skin diagnostic system 100A may also include a memory (not shown) as well as an input/output interface and devices 105, such as but not limited to, a display, computer keyboard and a mouse.

In some embodiments, as seen in FIGS. 1A and/or 1B, the one or more modules 107 may include, but are not limited to, a target skin data receive module 201, a target skin data analyze module 202, an operating parameter determine module 203, a treatment module 109 (FIG. 1B), and one or more other modules (not shown), associated with the skin diagnostic system. In some embodiments, the target skin data receive module 201 receives target skin data of the target skin being analyzed. In some embodiments, the target skin data analyze module 202 is used to analyze, parse and train the skin diagnostic system with training data. In some embodiments, the one or more skin treatment modules 109 are skin treatment models used to analyze, parse and output parameters to treat target skin. In some embodiments, there are preset operating parameters for the skin treatment system that comprise but are not limited to: the aesthetic skin treatment unit's technical specification limits, a safety parameter as a function of the intended treatment and/or clinical effect for a specific skin type of a patient, an area of skin that should not receive the treatment such as a "no-fire" zone, or any combination thereof.

In some embodiments, the one or more modules 107 are configured such that the modules gather and/or process data results are then stored in the memory of the skin diagnostic system, as part of data 108, such as training data, operating treatments parameters data or analyzed target skin data (not shown). In some embodiments, the data 108 may be processed by the one or more modules 107. In some embodiments, the one or more modules 107 may be implemented as dedicated units and when implemented in such a manner, the modules may be configured with the functionality defined in the present disclosure to result in a novel hardware device. As used herein, the term module may refer to an Application Specific Integrated Circuit (ASIC), an electronic circuit, a Field-Programmable Gate Arrays (FPGA), Programmable System-on-Chip (PSoC), a combinational logic circuit, and/or other suitable components that provide the described functionality. In some embodiments, the training data used to train the modules in successfully identifying of target skin attributes. In some embodiments, the unsuccessful identifying of target skin attributes is included for training a model.

In some embodiments, and as seen if FIG. 1B, the skin diagnostic system 100A is a combination skin diagnostic and an energy-based treatment system with a component for production of the energy-based treatment, and an additional component is a processor or controller component 102 (hereinafter PC component). The combination system 100A may also include input/output interface 105 and devices 105, such as but not limited to, a display, computer keyboard and a mouse. The PC component 102 may have two distinct processors connected to each other (not shown), and this connection may be an Ethernet cable. A first of the two processors may be configured with modules to; collect images; analyze the collected images with a plurality of trained models to produce skin attributes and instruct a flow to a user via an input/output module. A second of the two processors may be configured with modules to manage a graphical user interface (GUI) for the input/output modules, control the treatment energy, and analyze skin attributes with a skin treatment module to determine the treatment to be used.

In some embodiments, the combination system further comprises a module 210 configured to control obtaining the image data with an image capture device such as a multi-spectral camera which may be part of a handpiece 1300. In some embodiments, the combination system further comprises a treatment component with a handpiece to deliver the energy-based treatment 1350.

The target skin data, in some embodiments, includes skin attributes or at least one attribute of the target skin tissue to be analyzed. In some embodiments, the target skin data comprises at least one pre-treatment target skin attribute (pre-treatment target skin data), and at least one real-time target skin attribute (real-time target skin data). The pre-treatment target skin data may be skin attributes associated with the target skin before performed aesthetic treatment on the target skin. The real-time target skin data may be skin attributes which are obtained in response to real-time aesthetic treatment. In some embodiments, the target skin data is obtained before, during at regular intervals of time, and immediately after the aesthetic treatment or any combination thereof. The target skin data at any time around the aesthetic treatment may be analyzed to develop different treatment parameters. The treatment may be done in a short time period, such as a laser firing, and thus the gathering of image data and decision-making will desirably also be fast, i.e. capable of delivering feedback signals in less than few milliseconds.

In some embodiments, upon receiving the target skin data, the target skin analyze module 202 may be configured to analyze the target skin data using a plurality of trained models to determine a plurality of skin attributes of the target skin. In some embodiments, the plurality of trained models may be plurality of machine learning models, deep learning models or any combination thereof. Each of the plurality of trained models may be trained separately and independently. In some embodiments, each of the plurality of trained models may be pre-trained using the training data. In some embodiments, target skin data are associated with skin attributes, and includes but are not limited to melanin, an anatomical location, spatial and depth distribution (epidermal/dermal) of melanin, spatial and depth distribution (epidermal/dermal) of blood, melanin morphology, blood vessels morphology, veins (capillaries) network morphology diameter and depth, spatial and depth distribution (epidermal/dermal) of collagen, water content, melanin/blood spatial homogeneity, hair, temperature or topography.

Figure 2A:
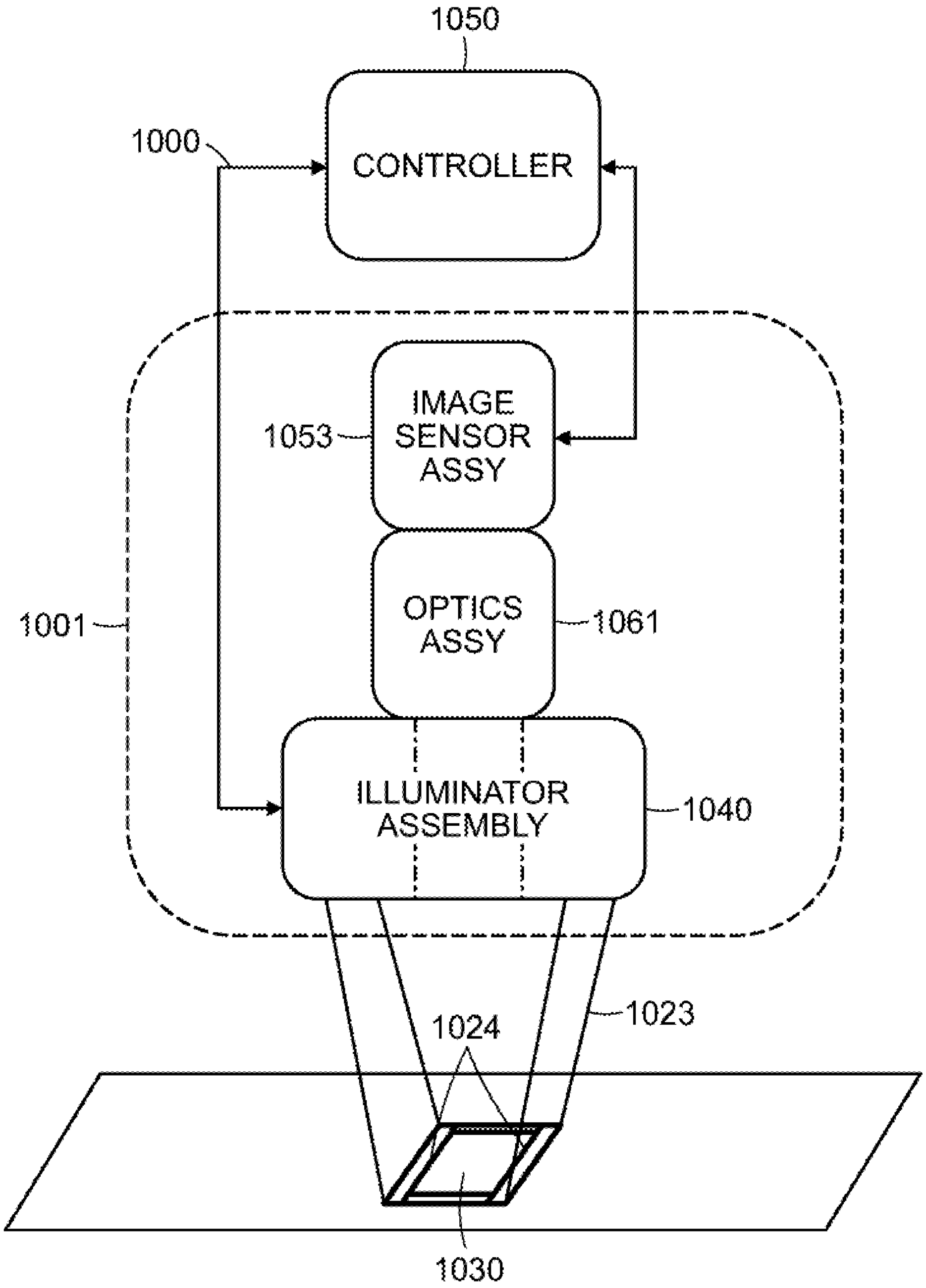
FIGS. 2A to 2C depict a diagram of an apparatus as part of the skin diagnostic system of the current invention.

FIG. 2A depicts a diagram of an apparatus 1000 as part of the skin diagnostic system for sensing and analyzing skin condition, according to some embodiments of the skin diagnostic system. The apparatus 1000 may be a diagnostic stand-alone unit (I.e., without an energy-based treatment source). According to some embodiments, the skin diagnostic system may also include an energy-based treatment source.

The apparatus may comprise a frame 1023, configured to circumscribe a target skin tissue 1030, to stretch or flatten the target skin tissue 1030 for capturing of diagnostic images. In some embodiments, target skin data includes diagnostic images captured of target skin 1030. The frame 1023 may comprise one or more fiducial markers 1024. The fiducial markers 1024 may be included in the images and used for digital registration of multiple images captured of the same target skin tissue 1030.

The apparatus may comprise an electro-optics unit 1001, comprising an illuminator assembly 1040, an optics assembly 1061, and an image sensor assembly 1053.

The illuminator assembly 1040 may be configured to illuminate the target skin tissue 1030 during capturing of images. The illuminator assembly 1040 may comprise a plurality of sets of one or more illumination elements also called illumination light sources (such as LEDs), each set having a different optical output spectrum (e.g., peak wavelength). A combination of one or more of the optical spectra may be employed for illumination when capturing images of the target skin skin tissue 1030. Images at each optical spectrum may be captured individually, and the images subsequently combined. Alternatively, or additionally, illumination elements, of the illuminator assembly, of multiple optical spectra may be illuminated simultaneously to capture an image. The optics assembly 1061 focuses the reflected/backscattered illumination light onto an image sensor of the image sensor assembly 1053.

The apparatus may further comprise a processor 1050 in the instant example, or processor 104 from previous figures. There may be more than one processor to the skin diagnostic system. The processor 1050 may be responsible for controlling the imaging parameters of the illuminator assembly 1040 and the image sensor assembly 1053. The imaging parameters may include the frame rate, the image acquisition time, the number of frames added for an image, the illumination wavelengths, and any combination thereof. The processor 1050 may further be configured to receive an initiation signal from a user of the apparatus (e.g., pushing of a trigger button) and may be in communication with a skin diagnostic system.

Figure 2C:
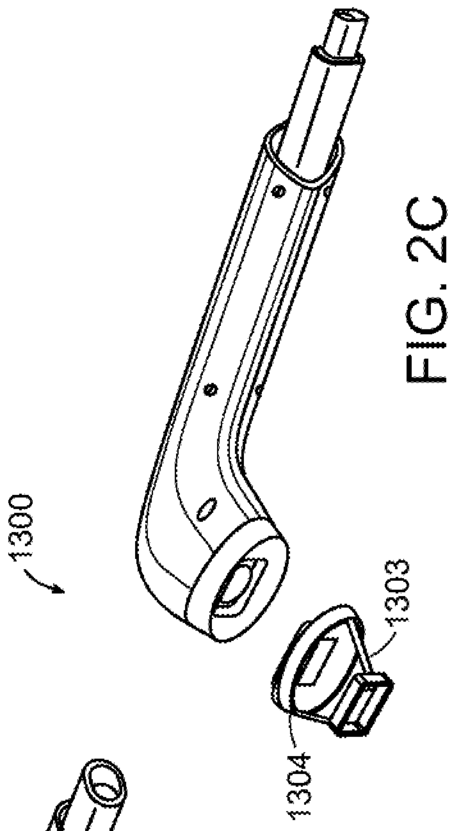
Figure 2B:
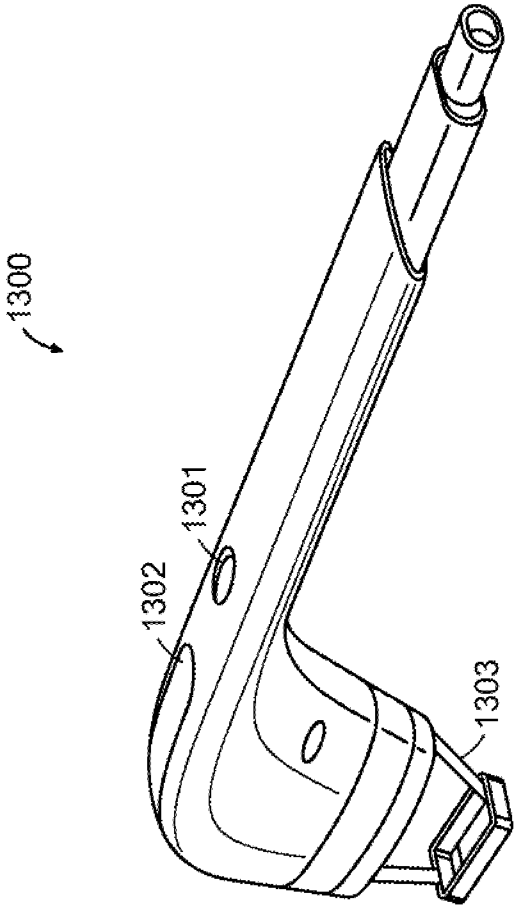

FIGS. 2B and 2C is a skin imaging handpiece 1300 according to some embodiments of the invention. In some embodiments, the skin imaging handpiece 1300 comprises a trigger button 1301, a heatsink 1302, and a frame 1303 including fiducial markers 1304. In some embodiments, the frame 1303 is removable from the skin imaging handpiece 1300, enabling interchanging between frames of various sizes or shape, in accordance with treatment indications. FIG. 2C shows the frame 1303 removed from the skin imaging handpiece 1300. Details on the system and method comprising a treatment component with a handpiece to deliver the energy-based treatment is further described in U.S. application Ser. No. 17/565,709 filed 30 Dec. 2021 and U.S. application Ser. No. 17/892,375 filed 22 Aug. 2022 which both are hereby incorporated by reference in their entirety.

Figure 3:
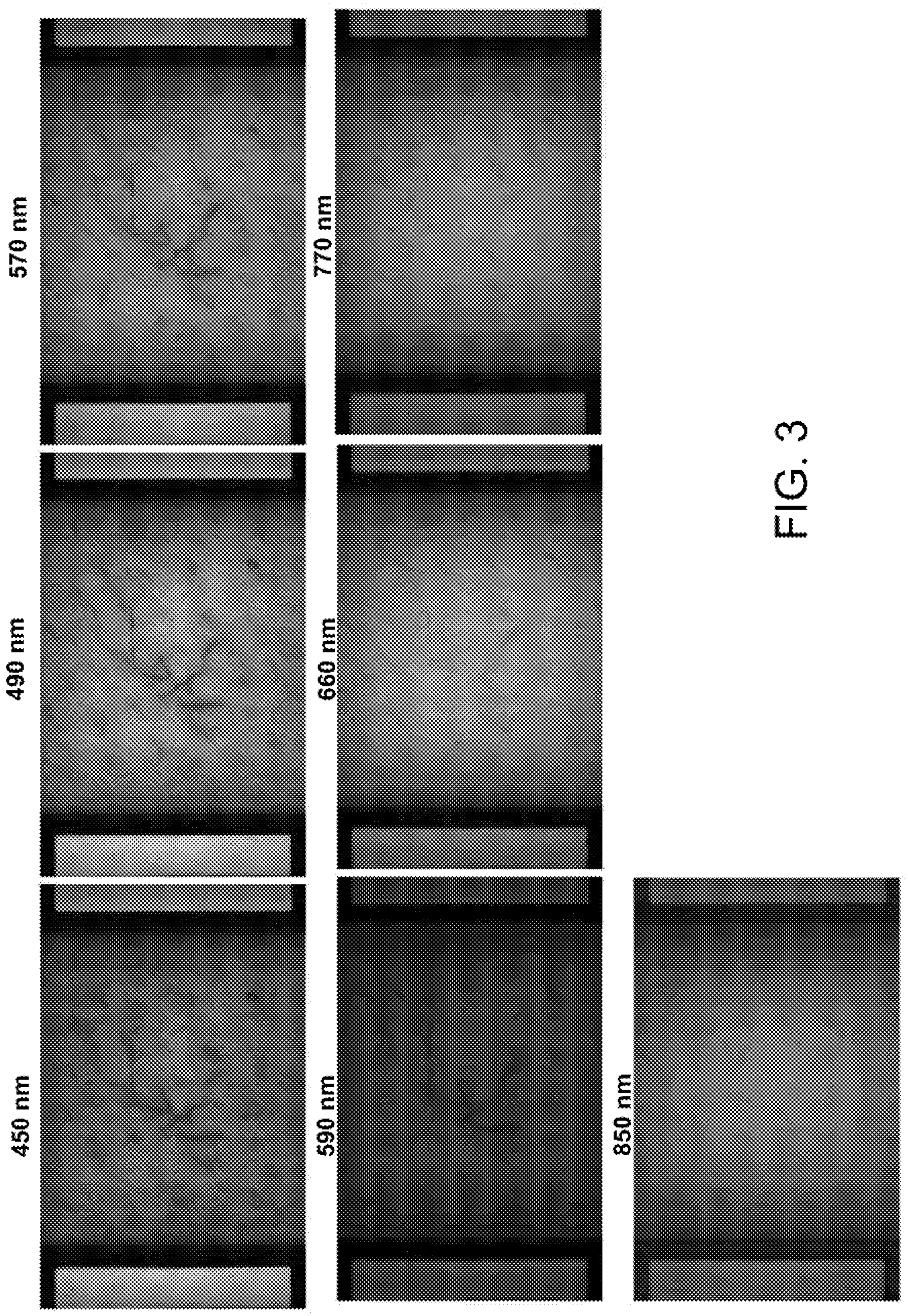
FIG. 3 illustrates a series of monochromatic images obtained by the system of the current invention.

FIG. 3 depicts that, in some embodiments, the skin diagnostic system has an image capture system that is configured to capture a plurality of monochromatic images by an image sensor at different peak wavelengths (hereinafter wavelengths). In some embodiments, there are seven monochromatic image captures each at a different wavelength, for example 450 nm, 490 nm, 570 nm, 590 nm, 660 nm, 770 nm, and 850 nm as seen in FIG. 3.

Pre-Processing

In some embodiments of the skin diagnostic system, there are a plurality of preprocessing methods for the Images captured. An image captured may be cropped or sized to the measurement of an energy-based treatment spot. Additional preprocessing functions that may be utilized are a quality check, an Illumination correction, a registration, and a reflectance calibration.

Figure 4B:
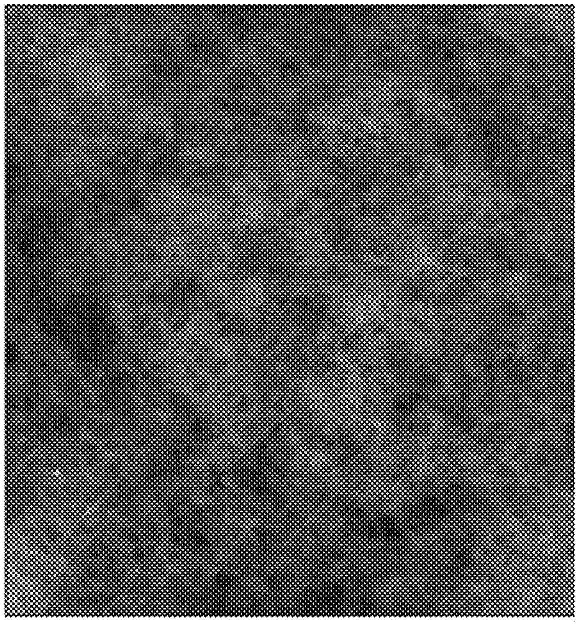
FIGS. 4A and 4B depicts the uneven illumination of an image and the correction as used in the current invention.
Figure 4A:
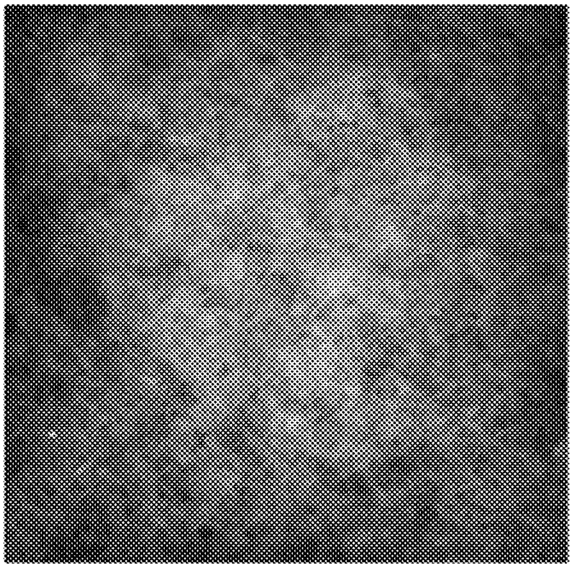

FIG. 4A illustrates an example of an image depicting uneven illumination and FIG. 4B an example of the corrected illumination image after a pre-processing illumination correction. Registration between all the monochromatic images aligns all the monochromatic images.

Reflectance calibration may be done in real time. The real time calibration may be done according to the following formula:

Calibrated Image=(1 registered image/2 calibration coefficient)×(marker calibration values/markers measured)

wherein the registered image is the plurality of monochrome images aligned with each other. The calibration coefficient is a plurality of reflectance values of each monochrome image from a reflective material that may be Spectralon®. An average of the plurality of reflectance values may be used as the calibration coefficient. The calibration coefficient is usually determined at time of manufacture of the skin diagnostic system. The marker calibration value refers to fiducial markers 1304. The same process of calibration coefficient is used except that the determination is done from cropped images of only the fiducial marker, also at the time of manufacture. The markers measure the real time current value of the calibration of the fiducial marker cropped image. After pre-processing, the incoming image data may then be parsed for input in a module or model.

Figure 4C:
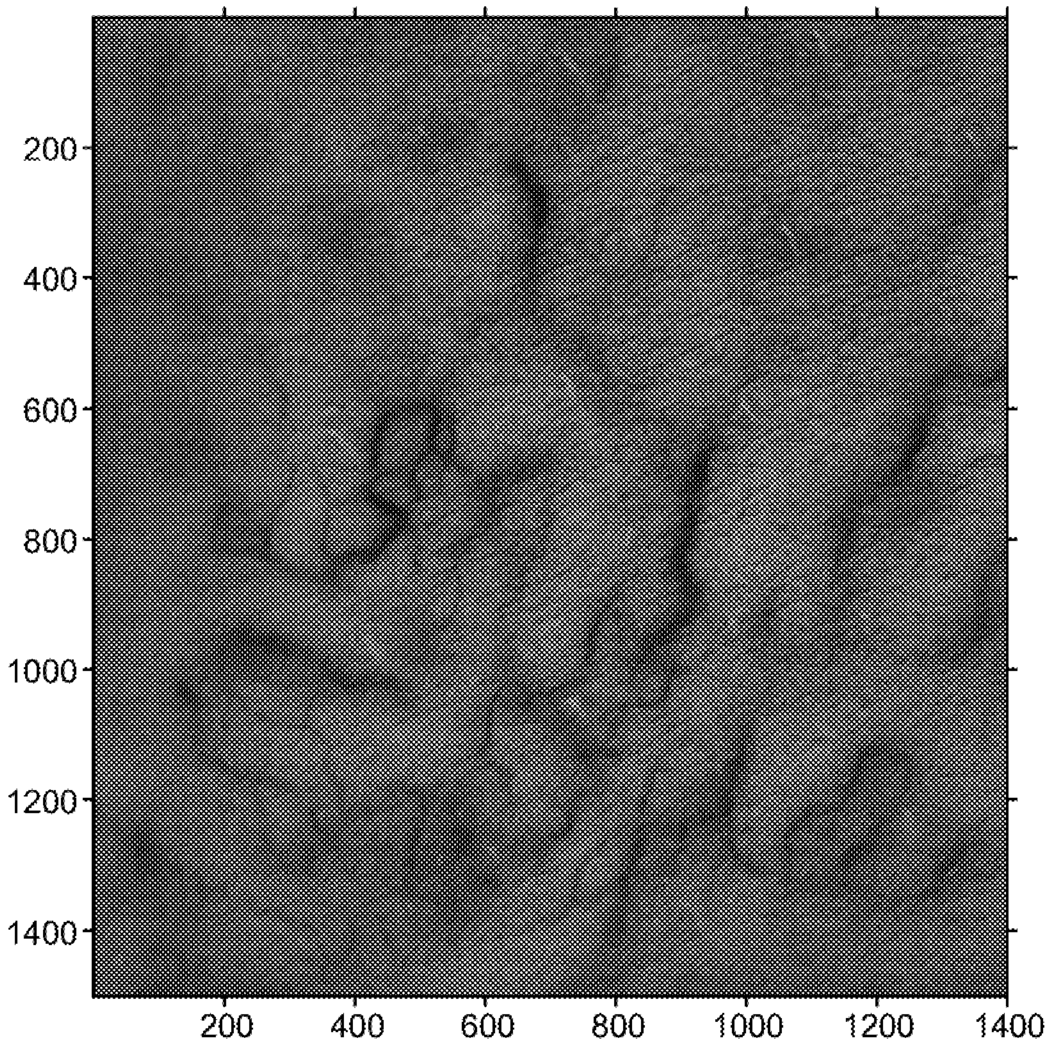
FIG. 4C depicts an enhanced view of blood vessels obtained by a combination of two images obtained at different wavelengths as an output of the current invention.

In some embodiments, the skin diagnostic system generates a color map or RGB image from the monochromatic images. The color map may be a 24-bit RGB image in a non-compressed or compressed image format. The construction of this image using the 650 nm wavelength, 570 nm wavelength and the 450 nm wavelength. In some embodiments, each wavelength used in the color map first has a global brightening step and a local contrast enhancement step performed before combining the wavelengths. In some embodiments, any monochrome images may be combined. Combinations of other wavelengths may have the effect of enhancing certain skin structures/conditions, as can be seen in FIG. 4C, two wavelengths are used to display an approximate blood vessel map.

Figure 5:
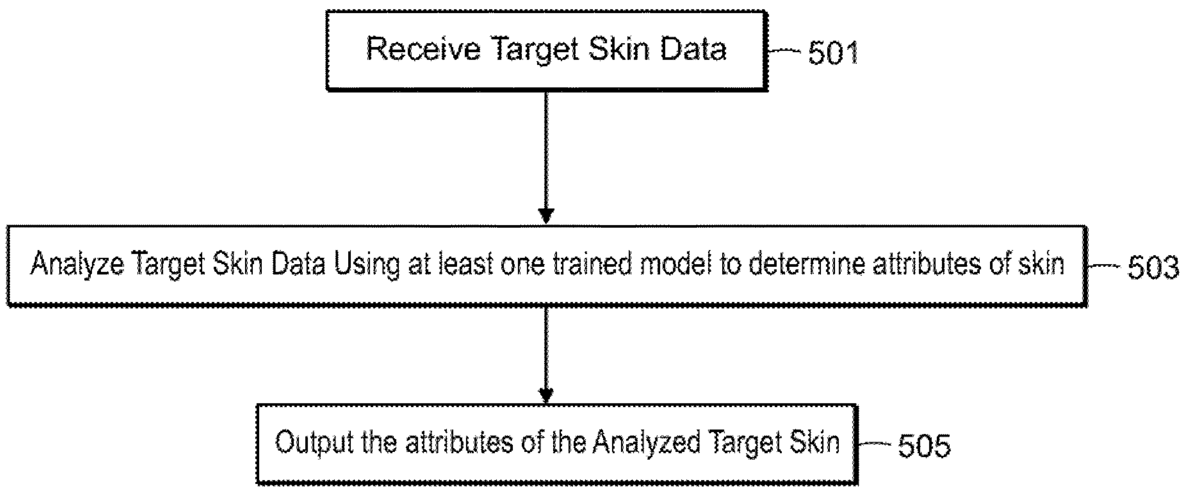
FIG. 5 is a flow chart depicting a method for determining attributes or characteristics of the target skin of the current invention.

FIG. 5 is a generalized flow chart depicting a method for determining the attributes or characteristics of the target skin.

At block 501, the skin diagnostic system is configured to receive the target skin data comprising multi-spectral images.

At block 503, the skin diagnostic system is configured to analyze the target skin data using at least one trained model to determine attributes of the target skin.

At block 505, the system is configured to output the skin attributes of the analyzed target skin. In some embodiments, these attributes are associated with skin conditions, skin diseases, skin reactions to treatment or any combination thereof.

Hair Mask

Figure 6:
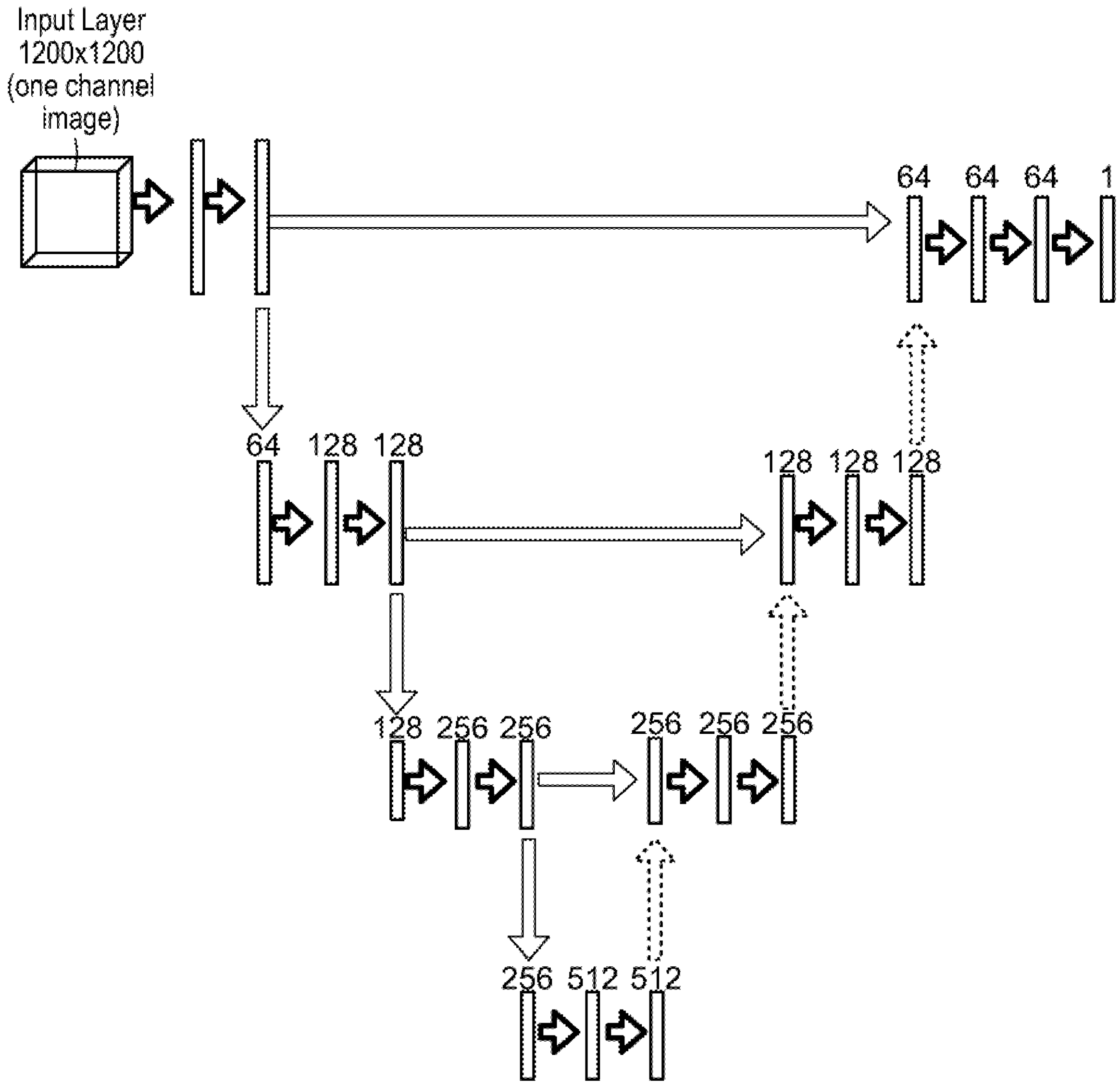
FIG. 6 illustrates one example of a machine learning model of the current invention.

In some embodiments, hair in the target skin data is automatically identified and removed (masked) from further analysis utilizing a hair mask module in the one or more modules 107. In some embodiments, a deep learning model for masking of hair is a U-Net deep learning semantic segmentation classifier model with a depth of three layers, by specific example see FIG. 6, hereinafter hair mask model. In some embodiments, the hair mask model is trained to detect, for each pixel of an image, hair, or background (everything but hair). In some embodiments, the hair mask model is trained with labeled target skin images by pixel labeling the hair in the target skin image.

Figure 7:
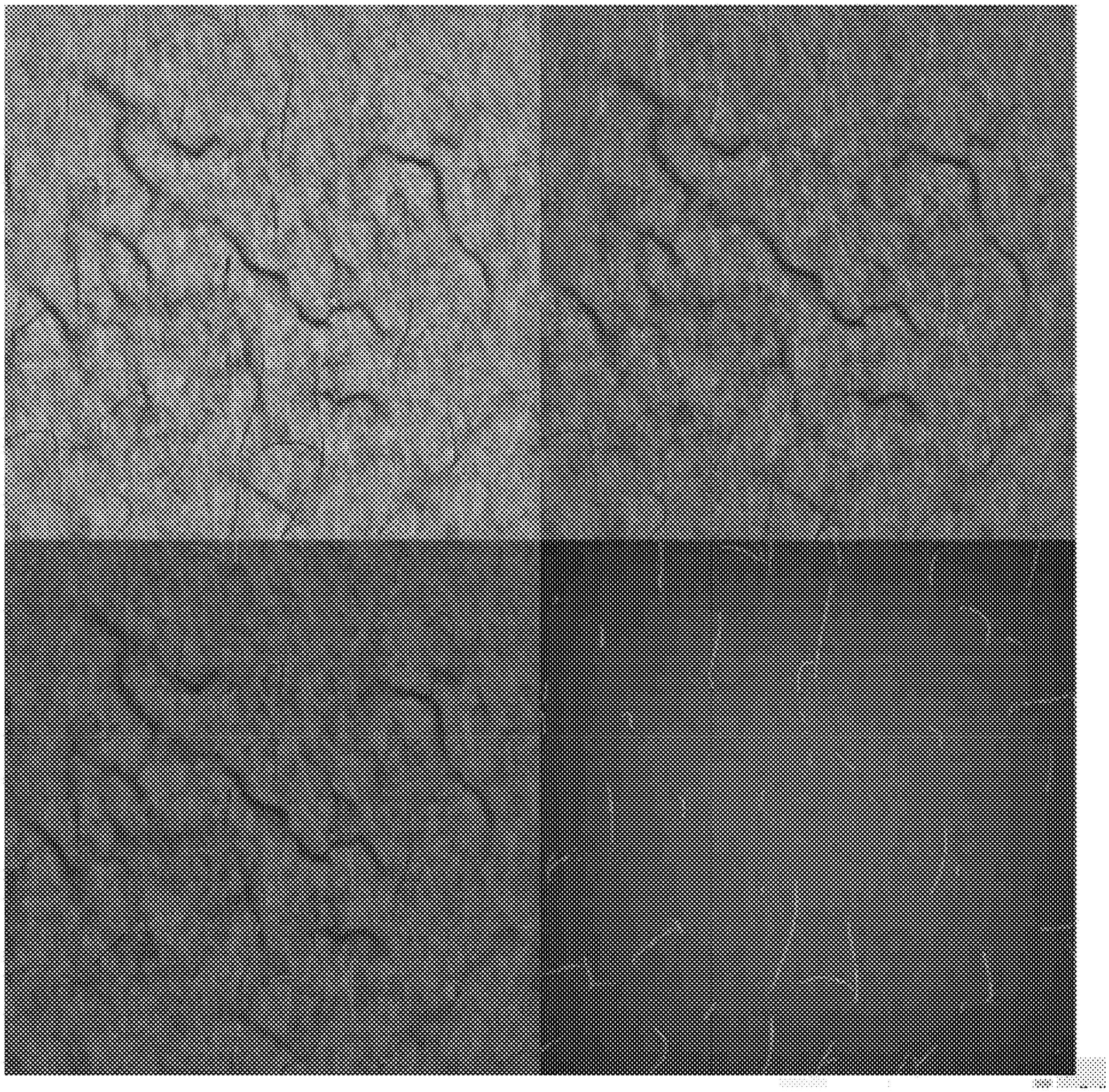
FIG. 7 illustrates an image output of a hair mask machine learning model of the current Invention.

In some embodiments, the hair mask model receives one monochromatic image of the target skin images. The one image may be a wavelength between about 590 nm to 720 nm. As seen in FIG. 7 and in some embodiments, the output of the hair mask model is the classification of hair or background in images and removing the hair from the target skin image and target skin data. In some embodiments, the removal of the hair from the target skin image and the target skin data removes the hair data and pixels from any further analysis of target skin, by instructing other models and modules in the skin diagnostic system to ignore pixels labeled by the hair mask model as being hair. In some embodiments, the hair mask data may be collected and stored in memory for further development of hair mask models.

Skin Type

In some embodiments, the skin type of a person's skin based on the Fitzpatrick scale is automatically determined by a skin type module in the one or more modules 107. The Fitzpatrick scale is a measure of the response of a skin to ultraviolet (UV) light and is one designation for the person's whole body. Typically, a trained medical professional makes such a determination. In some embodiments, the skin type module comprises machine learning multi-layer perceptron type neural network model, hereinafter akin type model. In some embodiments, the skin type model is trained with images of target skin labeled with the appropriate skin type numbered 1 to 6. In some embodiments, the images labeled for training were labeled by medical professional.

Figure 8:
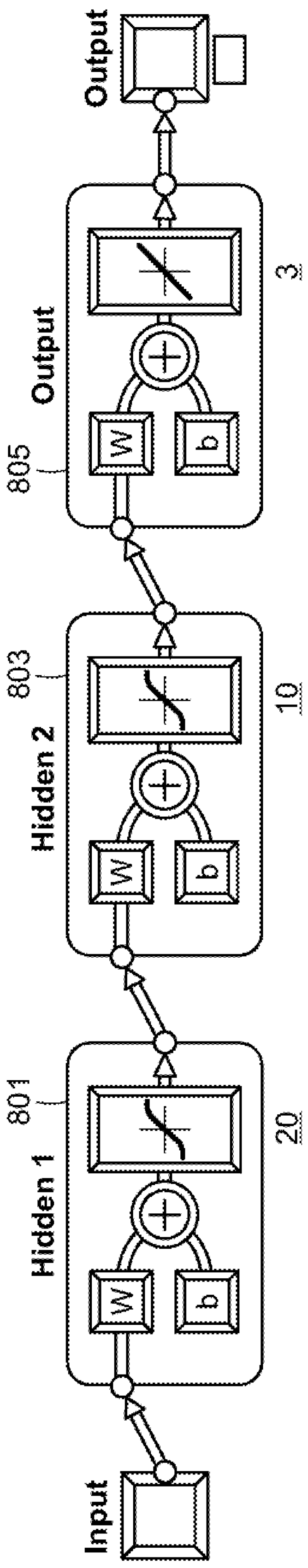
FIG. 8 illustrates a second example of a machine learning model of the current invention.

FIG. 8 is a non-limiting example of a multi-layer perceptron type of neural network with two hidden layers used in the skin type model that comprises; a first hidden layer with twenty neurons 801, a second hidden layer with ten neurons 803, and an output layer with three neurons 805. The neural network utilized in the skin type model may have a sigmoid, non-linear activation function, the output is a non-linear function of the weighted sum of input. Also typical of a neural network a W represents weight which is a parameter within a neural network that transforms input data within the network's hidden layers. B represents bias which is a constant value (or a constant vector) that is added to the product of inputs and weights of a neural network.

In some embodiments, the skin type model receives skin type data comprising an average calibrated reflectance value of the total pixels of each monochrome image [average spectrum of all the monochrome images] and the output of the skin type model is to classify the skin type into one of 6 skin types. Skin type data may be collected in a memory for further development of skin type models.

In some embodiments, the output is a skin type for the target skin to be treated and is automatically determined by a skin type module in the one or more modules.

Look Up Table-Skin Attributes

Reflectance images from skin tissue may be determined by two physical properties, chromophore absorption and reduced scattering of the induced illumination. Integration of those parameters through tissue depth yields the reflectance image. Thus, reflectance imaging (different wavelengths, polarizations, and patterns) provides information about the basic skin optical properties up to several millimeters in depth.

In some embodiments, skin attributes related to spectral analysis are automatically determined and generated. In some embodiments, look up tables (LUT) such as FIG. 9 are built employing known physical models of illumination effects on skin and generating a plurality of skin attribute values for skin models.

Figure 10:
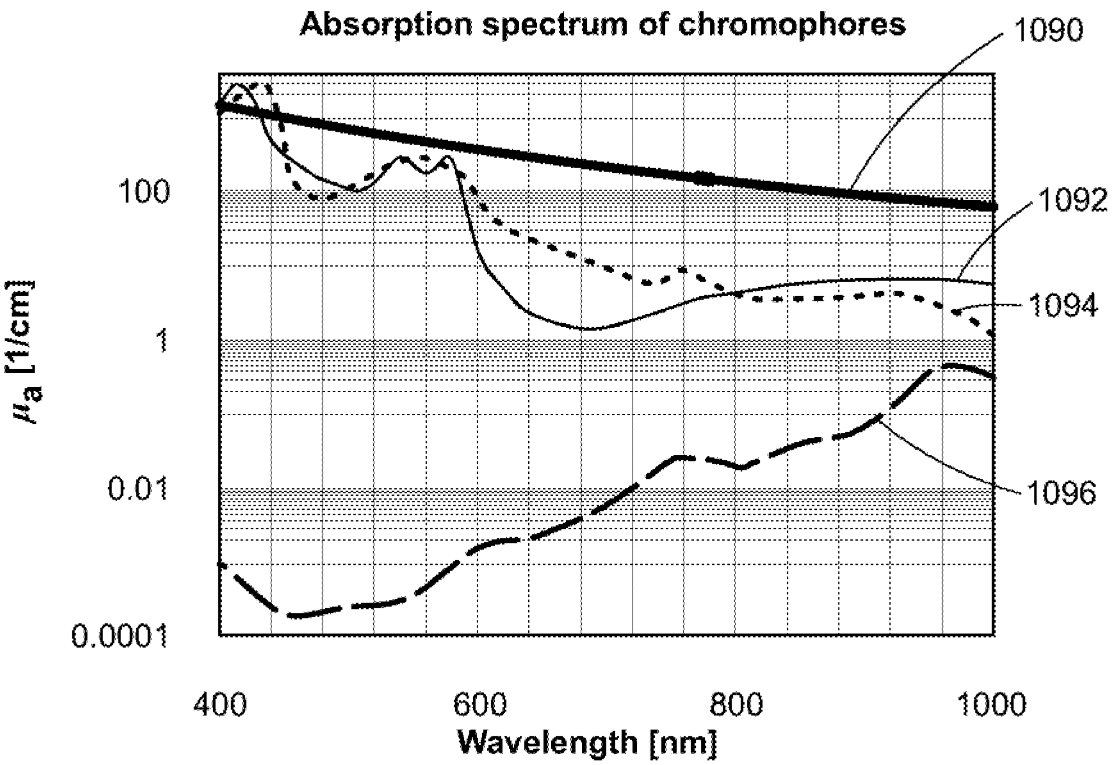
FIG. 10 is a graph of the absorption coefficients of the main chromophores in target skin as used in the current invention.

The skin attribute values may include, but are not limited to, melanin (pigment) density, vascular (erythema) density, and coefficient of scattering of light. In some embodiments, physical equations and spectral analysis are used to complete the LUT with the skin attributes per wavelengths. FIG. 10 illustrates a graph of the absorption coefficients of the main chromophores in the target skin, which are melanin 1090, hemoglobin with 1092 and without 1094 oxygen, and water 1096, as a function of the wavelength of illumination. Along with physical models of light scattering in human skin, it provides the base for completing the LUT. Further, the LUT values represent the physical measure of concentration in a volume of human skin of the skin attribute, for example if melanin is determined at 0.06 then the concentration of melanin is 0.06 percent.

In some embodiments, a machine learning model receives the image skin data and links the spectral wavelength response to skin chromophore quantities. In some embodiments this may be other skin chromophore (color producing areas of molecules) quantities, such as but not limited to vascular areas, melanin areas and collagen.

Each pixel of each of a plurality of wavelength images is input to a machine learning model to search on the LUT. Each of the plurality of skin attribute values and maps utilize a different machine learning model (hereinafter generic model) to determine each skin attribute value on target skin. For example, when seven wavelength images are employed, seven numbers for each pixel are inputted into the generic model to obtain an output of one number for each pixel. A brute force or naïve searching in a long LUT would typically analyze each line of the table and is very slow and time consuming, especially for each pixel in multiple monochrome wavelength images. Therefore, the generic model is utilized for faster and more efficient function in using the LUT.

Optionally, the generic models that use the LUT output an estimated value of a particular LUT skin attribute in the target skin for each pixel. In some embodiments, once the estimate for each pixel is determined, anomalous or outliers of the LUT skin attribute are identified. In some embodiments, the anomalous level of the LUT skin attribute is determined by the equation: Anomalous level≥Mean (LUT skin attribute)+c×STD (LUT skin attribute), where c is an arbitrary coefficient, for example 2. In some embodiments, the coefficient is determined experimentally by analyzing the distributions of the LUT skin attribute in a large number of images. The coefficient is different for each of LUT skin attributes. The non-anomalous levels are then classified, and normal skin and the anomalous levels are identified as the specific LUT skin attribute density.

Optionally, a basic map is generated illustrating the areas of the LUT skin attribute with anomalous levels and a corresponding color bar. In some embodiments, the scale of the map is adjusted such that the 0-15% range is mapped into 0-255 digital levels for display of the map. In some embodiments, the anomalous level pixels are compared to the total number of pixels to determine the relative area of the anomalous region. For example, LUT Skin Attribute Value=Total Pixels with anomalous values in Map/Total Pixels in image Displayed Units: % of image area (0-100%)

In some embodiments, the generic models are trained using a plurality of pixels from the image skin data on the LUT data to determine the attributes in target skin to be identified. The machine learning models for specific skin attributes will be further discussed below.

Melanin Density

Figure 11:
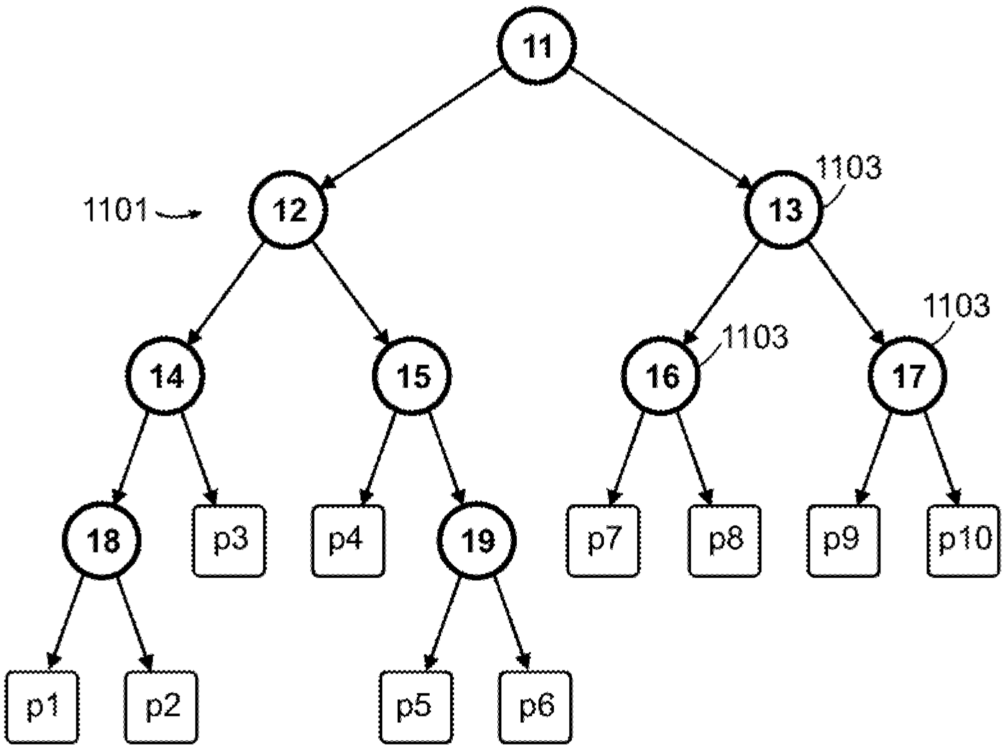
FIG. 11 illustrates a third example of a machine learning model of the current invention.

In some embodiments, utilizing the LUT, a melanin density and map is automatically determined by a melanin module in the one or more modules 107. In some embodiments, machine learning model for melanin density and mapping is a machine learning regression tree model for identifying melanin, hereinafter a melanin tree model, an example of which is seen in FIG. 11. By way of specific example, the melanin tree model has a tree depth of 25 layers (see 1101 as an example) and 132 leaves (see 1103 as an example.) The LUT discussed above is used by the melanin tree model to determine the melanin density and generate a melanin map.

In some embodiments, the melanin tree model receives the image skin data per pixel with a plurality of absolute reflectance values representing the plurality of wavelengths imaged. The melanin tree model then analyzes the plurality of absolute values per pixel compared to the LUT values and identifies for each pixel the one LUT entry with the value closest in distance to the plurality of measured absolute values for each pixel. This distance may be a similarity of certain distances such as, for example, cosine, Euclid distance, or any combination thereof.

Figure 13A:
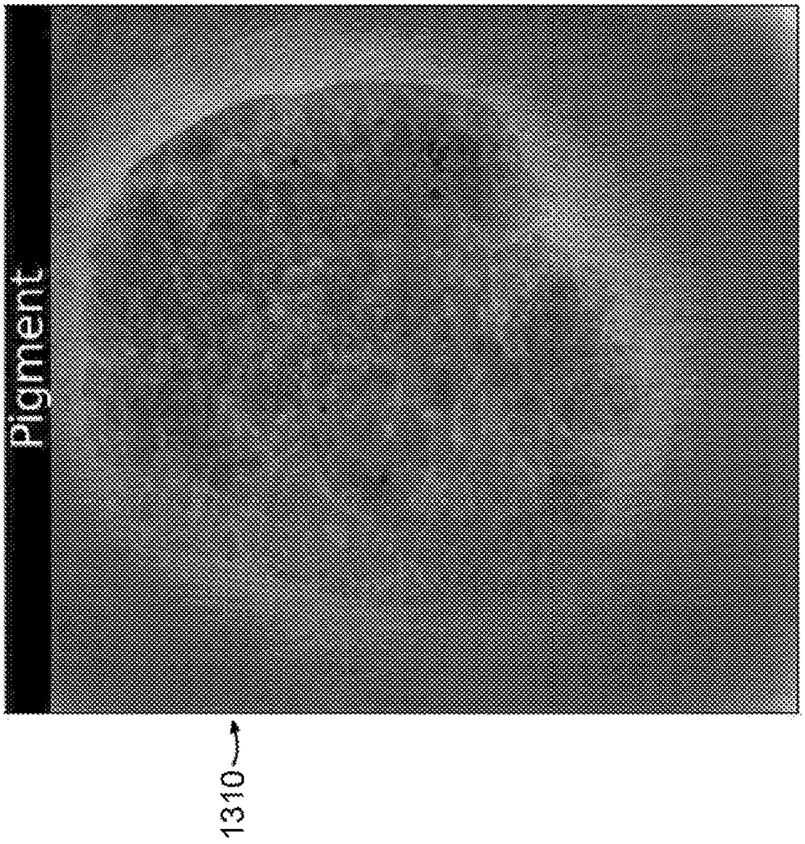
FIGS. 13A and 13B depict a map of melanin/pigment and vascular/erythema density as an output of the current invention.

In some embodiments, a map of the melanin density as illustrated in FIG. 13A, 1310 is produced from multiple wavelengths, for example, seven wavelengths, by determining value closest in distance to the measured values using the similarity of certain distances as already described above. Next, in some embodiments, the processor computes based on a computer program the value in the LUT which best represents the melanin density value already determined (See FIG. 12, 1203) while the other skin attributes on the LUT are closest to zero. In FIG. 12, the vascular value is the other skin attribute. The line of the LUT with the closest value for melanin and where other skin attributes are closest to zero is used to represent the RGB map of melanin. In the current example that is line 1205 of FIG. 12.

Vascular Density

In some embodiments, utilizing the LUT, a vascular density and map is automatically determined by a vascular module in the one or more modules 107. In some embodiments, machine learning model for vascular density and mapping is a machine learning regression tree model for identifying vascular areas, hereinafter vascular tree model. By way of specific example, the vascular tree model has a tree depth of 41 layers (see 1101 of FIG. 11 as an example) and 35,855 leaves (see 1103 of FIG. 11 as an example.) The LUT is used also by the vascular tree model to determine the vascular density and generate a vascular map.

In some embodiments, and similar to the melanin tree model above, the vascular tree model receives the image skin data and links the spectral wavelength response to skin chromophore quantities, in this case to vascular density.

In some embodiments, the vascular tree model receives the image skin data per pixel with a plurality of absolute reflectance values representing a plurality of wavelengths imaged. The vascular tree model then analyzes the plurality of absolute values per pixel compared to the LUT values and identifies for each pixel the one LUT entry with the value closest in distance to the plurality of measured absolute values for each pixel. This distance may be a similarity of certain distances such as for example cosine, Euclid distance, or any combination thereof.

Figure 13B:
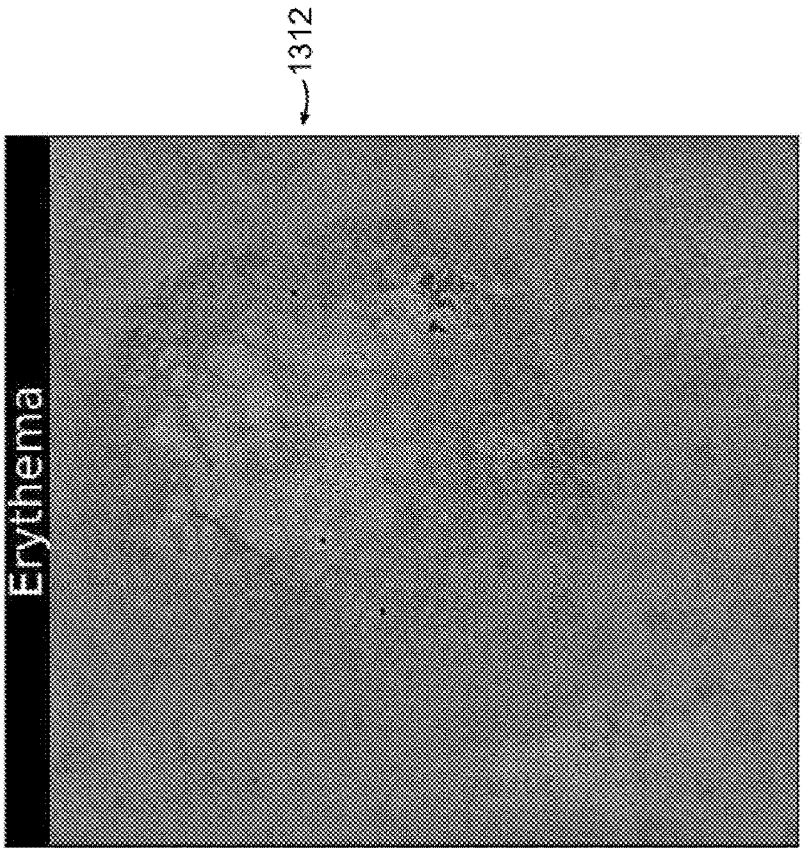

In some embodiments, a map of the vascular density, as illustrated in FIG. 13B, 1312, is generated from multiple wavelengths, for example seven wavelengths, by determining value closest in distance to the measured values using the similarity of certain distances as already described above. Next, in some embodiments, the processor computes based on a computer program the value in the LUT which best represents the vascular density value already determined while the other skin attributes on the LUT are closest to zero. The line of the LUT with the closest value for vascular density and where other skin attributes are closest to zero is used to represent the RGB map of vascular density.

Scattering

In some embodiments, also utilizing the LUT, a scattering light value is automatically determined by a scattering module in the one or more modules 107. In some embodiments, machine learning model for scattering light value is a machine learning regression tree model for identifying scattering attributes of the target skin, hereinafter scattering tree model. By way of specific example, the scattering tree model has a tree depth of 35 layers, and 81,543 leaves. The LUT discussed above is used by the scattering tree model to generate the scattering value.

In some embodiments, the scattering tree model receives the image skin data per pixel with a plurality of absolute reflectance values representing multiple wavelengths imaged.

The scattering tree model then analyzes the plurality of absolute values per pixel compared to the LUT values and identifies for each pixel the one LUT entry with the value closest in distance to the plurality of measured absolute values for each pixel. This distance may be a similarity of certain distances such as for example cosine, Euclid distance, or any combination thereof.

In some embodiments, skin chromophore estimations predict treatment energy absorption to predict treatment outcome (assuming known melanin/pigment and blood response to energy/temperature). In some embodiments, the output values and maps for melanin density, vascular density and scattering light may be collected in a memory for further development of machine learning models.

Example Utilizing LUT

Figure 14A:
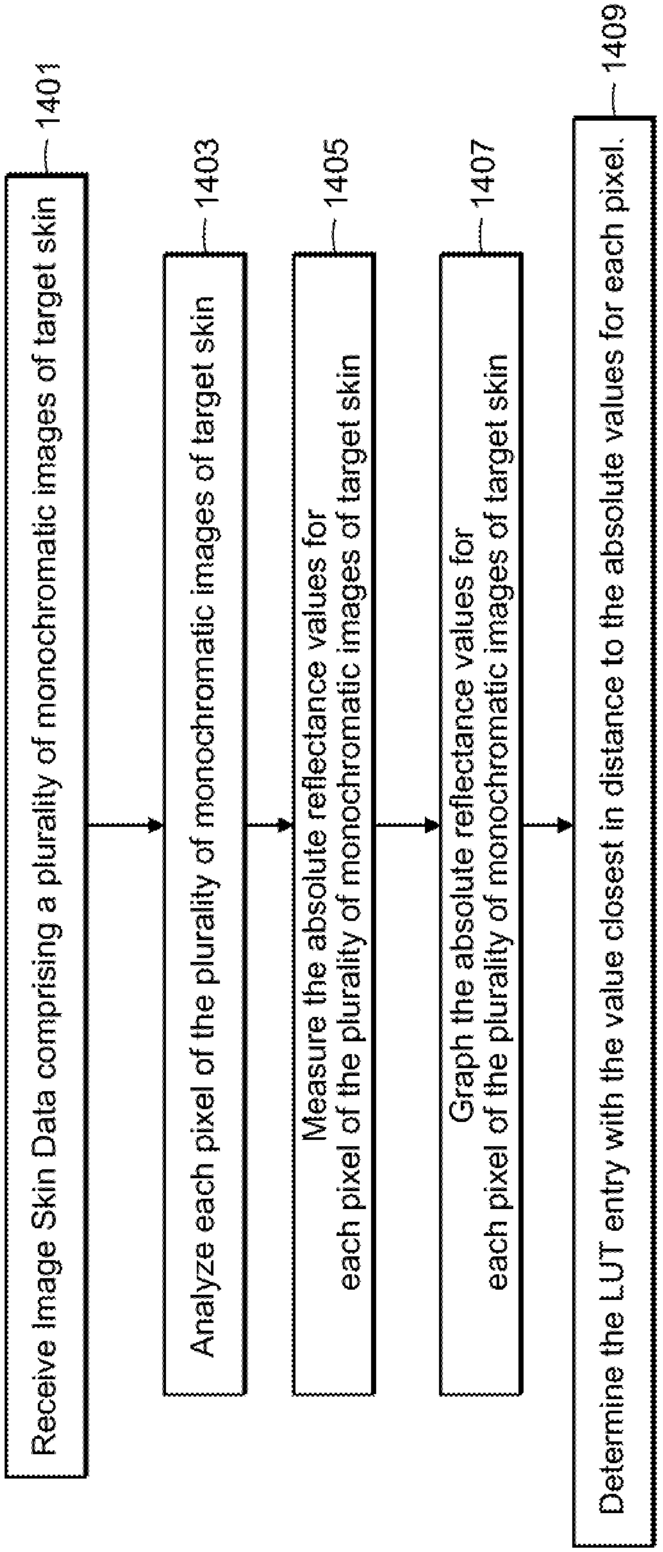
FIG. 14A is a flow chart depicting a method for determining attributes or characteristics of the target skin using a look up table (LUT) of the current invention.

FIG. 14A is a flowchart depicting a method for one of the machine learning models that employ the LUT to determine a specific skin attribute value on the LUT table for each pixel.

At block 1401, the skin diagnostic system is configured to receive image skin data comprising a plurality of monochromatic images of target skin.

At block 1403, the skin diagnostic system is configured to analyze each pixel of the plurality of monochromatic images of target skin.

At block 1405, the system is configured to measure the absolute reflectance values for each pixel of the specific skin attribute value sought of the plurality of monochromatic images of target skin.

At block 1407, the system using the machine learning modules is configured to graph the absolute reflectance values for each pixel to the one value for the same pixel represented in the LUT.

At block 1409, the system is configured to determine the LUT entry with the value closest in distance to the absolute values for each pixel.

Figure 14B:
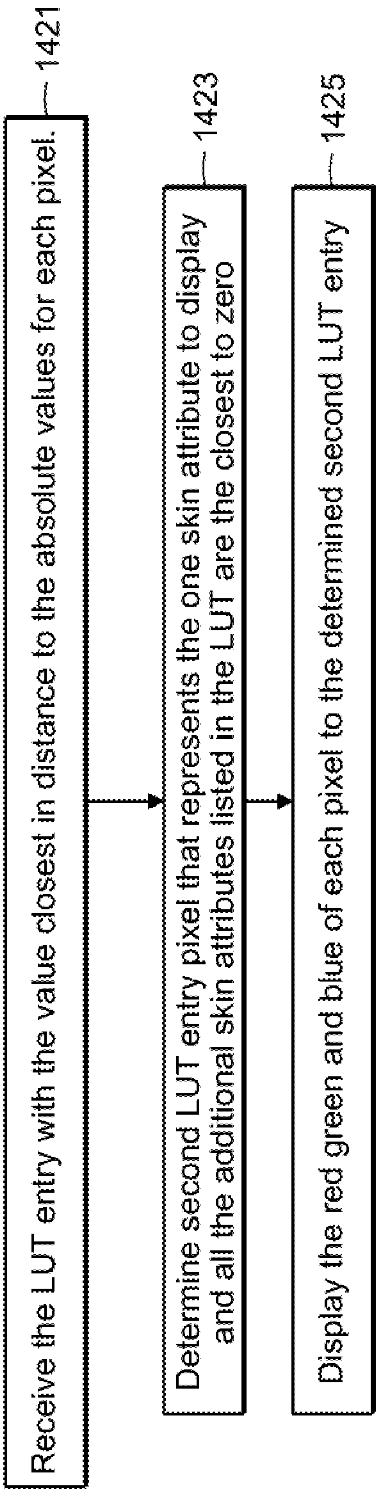
FIG. 14B is a flow chart depicting a method for generating a RGB map with the LUT that depicts attributes or characteristics of the target skin of the current invention.

FIG. 14B is a flow chart depicting a method to produce an RGB map of the skin attributes determined on the LUT.

At block 1421, the skin diagnostic system is configured to receive the LUT entry with the value closest in distance to the absolute values for the specific skin attribute sought for each pixel.

At block 1423, the skin diagnostic system is configured determine a second LUT entry value for each pixel that represents the one skin attribute to display and also sets all the additional skin attributes listed in the LUT closest to a value to zero.

At block 1425, the system is configured to generate a display of the red, green, and blue wavelengths of each pixel to the determined second LUT entry value.

Vascular Lesion Depth Map

In some embodiments, vascular lesion depth map is automatically determined and generated by a vascular depth module in the one or more modules 107. In some embodiments, a deep learning model for vascular depth determination is a U-Net deep learning semantic segmentation classifier model with a depth of four layers, hereinafter vascular depth model. In the current disclosure, a vascular lesion is a vascular structure apparent to the human eye. In some embodiments, the vascular depth model is trained to detect four classifications per pixel utilizing all the monochromatic images of image data. In some embodiments, the four classifications are deep depth vascular lesion, medium depth vascular lesion, shallow depth vascular lesion, and background.

In some embodiments, the vascular model is trained with labeled target skin images and each pixel labeled with the classifications in the target skin image, by way of specific example four classifications. In some embodiments, the target skin images are labeled for training with the classifications by experienced medical personnel.

In some embodiments, the vascular depth model receives a plurality of monochromatic images of the target skin data. In some embodiments, the output of the vascular depth model is an array with the image in four classifications of scores for matching each of the trained classes. In some embodiments, the vascular depth model further analyzes a four probabilities matrix (the output for the four classifications) by processing the relevant three probability layers into three possibilities matrix, that is, three depths of vascular lesions. In some embodiments, the three possibilities matrix is utilized by the vascular depth model for further analysis, and the output is the model probabilities of three classes: shallow, medium (not shallow nor deep) and deep vascular lesions. The classification with the maximal score may be chosen to be the predicted class for that pixel. In some embodiments, vascular structure lesion data may be collected in a memory of the skin diagnostic system for further development of the vascular depths models.

Figure 15:
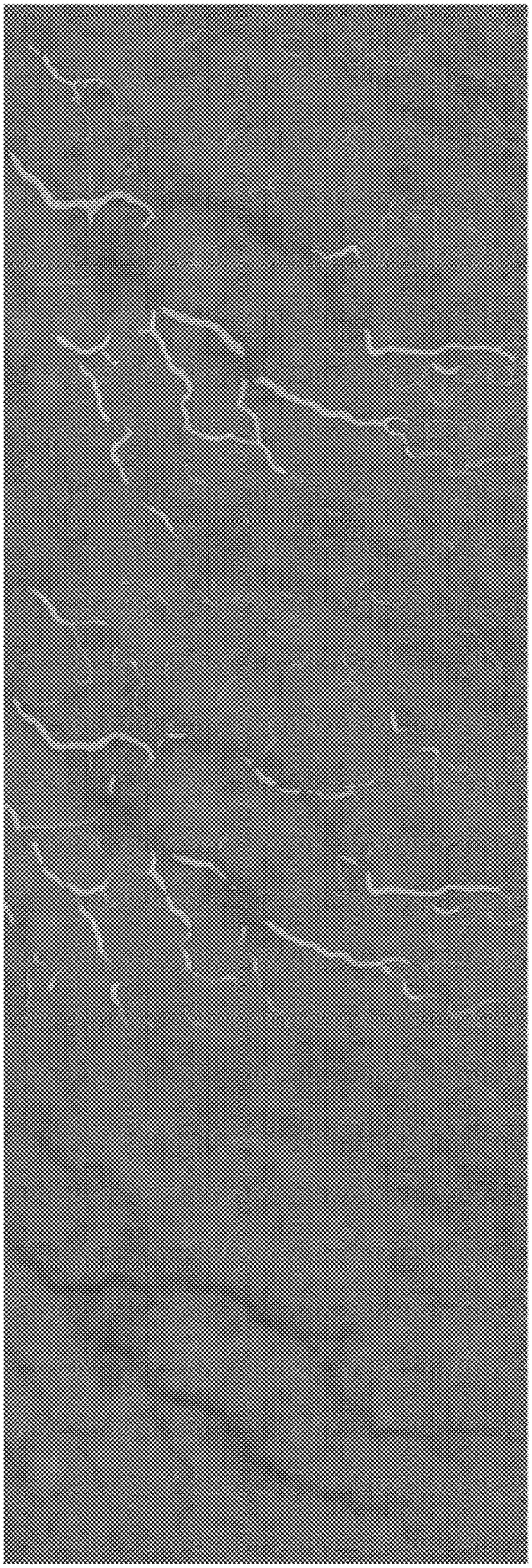
FIG. 15 depicts vascular lesion depth map as an output of the current invention.

In some embodiments, a vascular lesion depth map, is generated by the vascular depth model comprising a semi-transparent RGB or greyscale map overlaid with marking of vascular lesions segmented into shallow, medium, and deep. In some embodiments, the vascular module determines which pixels to mark in either of the three colors or markings. The vascular lesion depth map may use different colors or other markings to denote the depths of vascular lesions as seen in FIG. 15

In some embodiments, a depth determination as one of shallow, medium, or deep is determined automatically for the single image of the vascular lesion map by a one label vascular lesion module in the one or more modules 107.

In some embodiments, the one label vascular lesion model is trained with labeled target skin images labeled as an image with the classifications. In some embodiments, the target skin images are labeled with the classifications by experienced medical personnel.

Each pixel label outputted by the vascular module is received into the one label vascular lesion module. The one label vascular lesion module is a machine learning classifier model and outputs a single label for the image of shallow, medium, or deep.

Pigment Lesion Depth Map

In some embodiments, a pigment lesions depth map is automatically determined and generated by a pigment depth module in the one or more modules 107. Typically, a pigment lesion is an abnormal level of melanin based on a person's skin type. In some embodiments, pigment depth module comprises a machine learning 1D classifier model, hereinafter a pigment depth model. In some embodiments, pigment depth model is trained with images labeled by trained medical personnel as either "epidermal" (shallow) or "junctional" (deep) pigment lesions.

In some embodiments, the pigment depth model receives results from a vascular depth model and a hair mask model, removing the hair and vascular lesion information for each pixel from the pigment depth module analysis. Thus, the removal of the hair and vascular lesion from images and data removes hair and vascular lesion pixels from any further analysis of target skin, by instructing other modules and/or models to ignore those pixels.

In some embodiments, the pigment depth model receives measured brightness intensity per pixel of an image at two wavelengths. Typically, a low wavelength value such as 450 mm captures an image shallower in the target skin and a high wavelength value such as 850 mm captures an image deeper in the target skin. Also, typically pigment/melanin absorbs light (attenuates the amount of reflected light) resulting in darker image regions.

In some embodiments, the low wavelength value image is analyzed per pixel by the pigment depth model for determination of pigment lesions and if pigment lesions are present in the pixel, it is labeled as shallow pigment lesion pixel. In some embodiments, the high wavelength value image is analyzed per pixel by the pigment depth model for determination of pigment lesions and if pigment lesions are present in the pixel, it is labeled as deep pigment lesion pixel.

In some embodiments, pigment lesion pixels are determined in either wavelength value by brightness values assigned to each pixel with 255 brightness value representing white and a zero value representing darkness. In some embodiments, the pixel outliers for darkness are identified using standard deviation calculations. In some embodiments, the pigment depth model identifies outlier brightness intensity pixels by means of statistical analysis of the distribution of intensity levels in a standard deviation. The pigment depth model then may identify a threshold to classify the outliers as pigment lesions present in the target skin. In some embodiments, more than two depths of the pigment lesions may be classified.

Figure 16B:
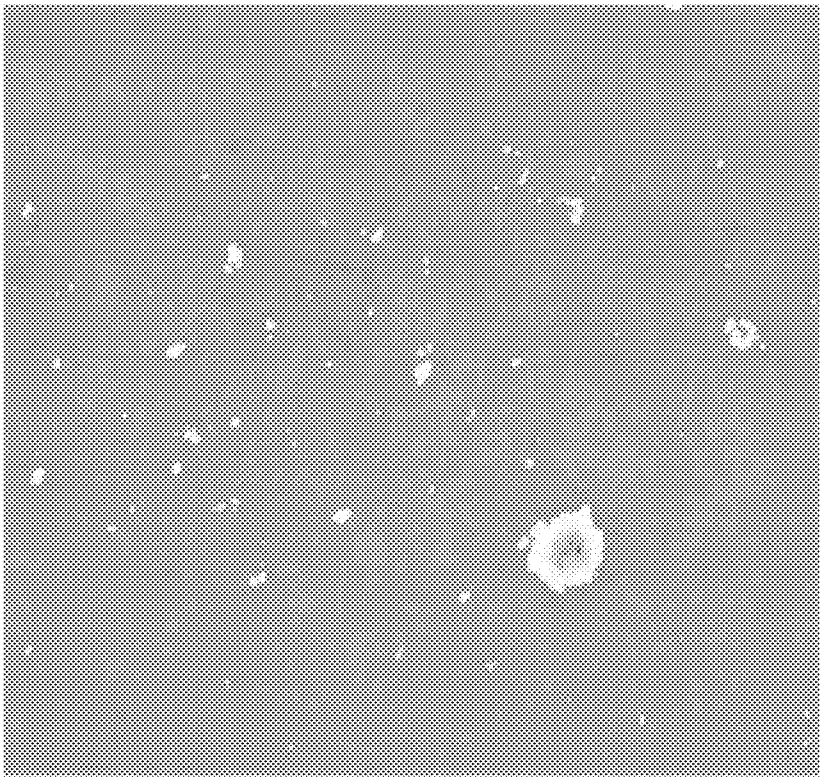
FIGS. 16A and 16B depict melanin lesion depth map as an output of the current invention.
Figure 16A:
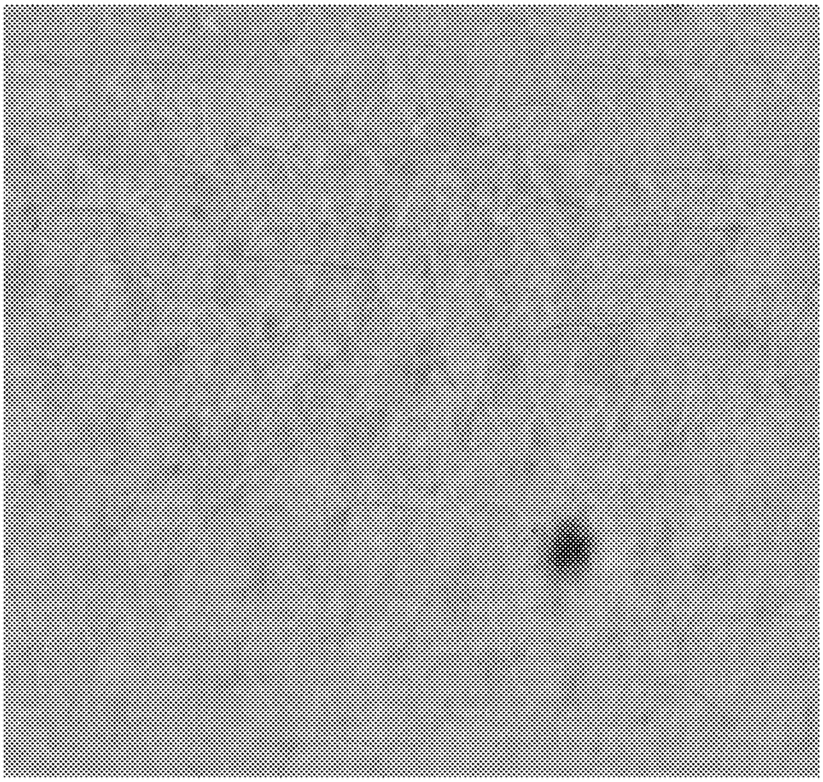

In some embodiments of the skin diagnostic system, a pigment lesion depth map is generated using the outlier pixels in each image of the lowest and highest value wavelengths. The pigment lesion depth map may use different colors or other markings to denote the depths of pigment lesions as seen in FIG. 16B. Outlier pixels on in the lowest wavelength image will be marked as deep pigment lesions and outlier pixels identified in the highest wavelength image will be marked as a shallow depth pigment lesions. In some embodiments, the pigment lesion data is collected in a memory for further development of pigment depth models.

In some embodiments, the pigment depth model receives a plurality monochromatic image of the target skin data and does not require input of the vascular depth model. In some embodiments, the output of the pigment depth model is an array with the image in four classifications of scores for matching each of the trained classes. In some embodiments, the pigment depth model further analyses a four probabilities matrix (the output for the four classifications) by processing the relevant three probability layers into three possibilities matrix and background, that is three depths of pigment lesions. The output is the model probabilities of three classes: epidermal (shallow), junctional (now medium) or dermal (deep) lesions. The classification with the maximal score may be chosen to be the predicted class for that pixel.

Vascular Lesion and Melanin Lesion Depth Map

In some embodiments, the vascular depth map and the melanin depth map are combined automatically by the skin diagnostic system. The output of the vascular depth model generated vascular lesion map and the pigment depth module pigment lesion map are combined per pixel by the system.

Figure 17A:
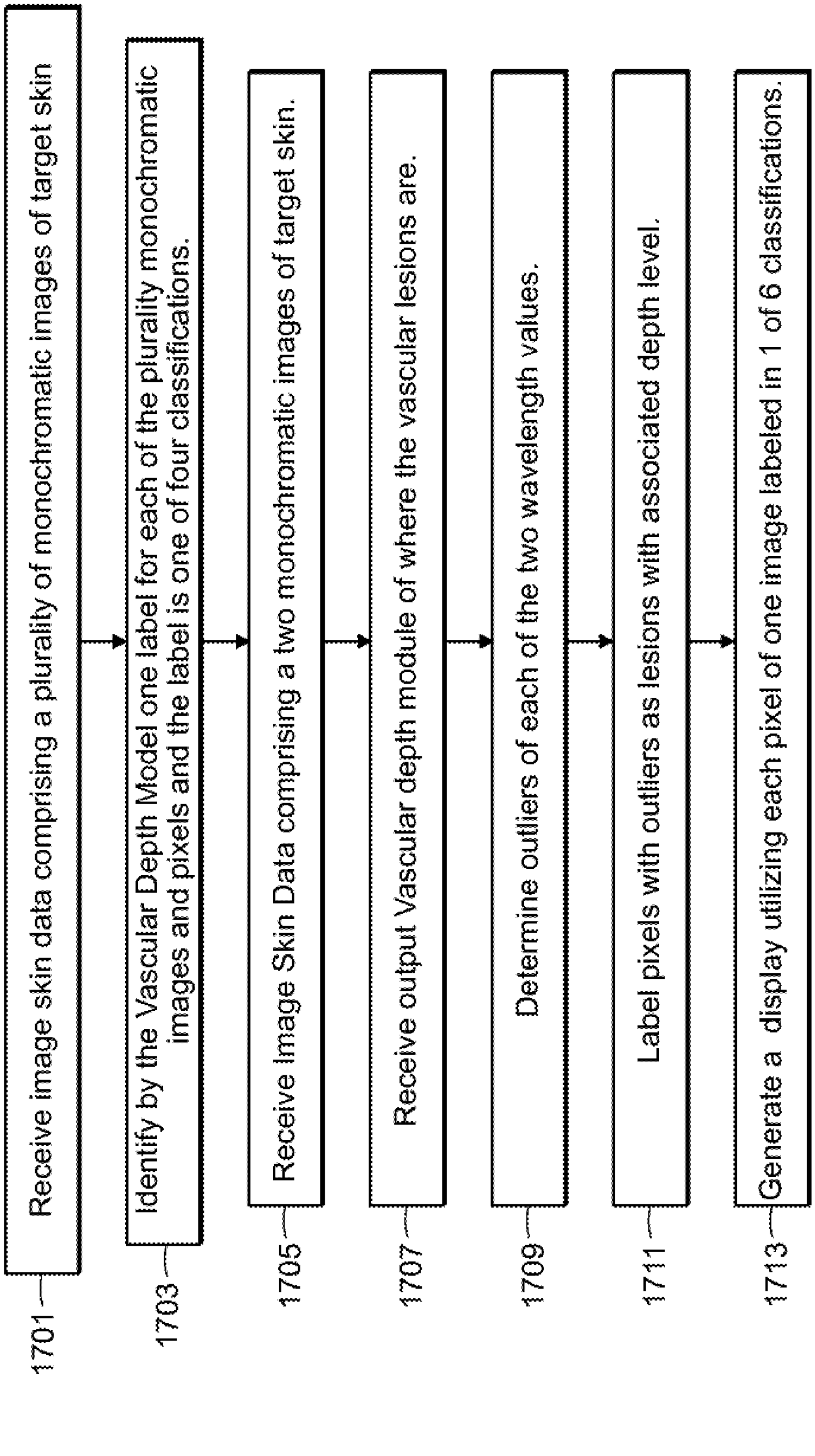
FIG. 17A is a flow chart depicting a method for generating a combined pigment and vascular lesion map of the current invention.
Figure 17B:
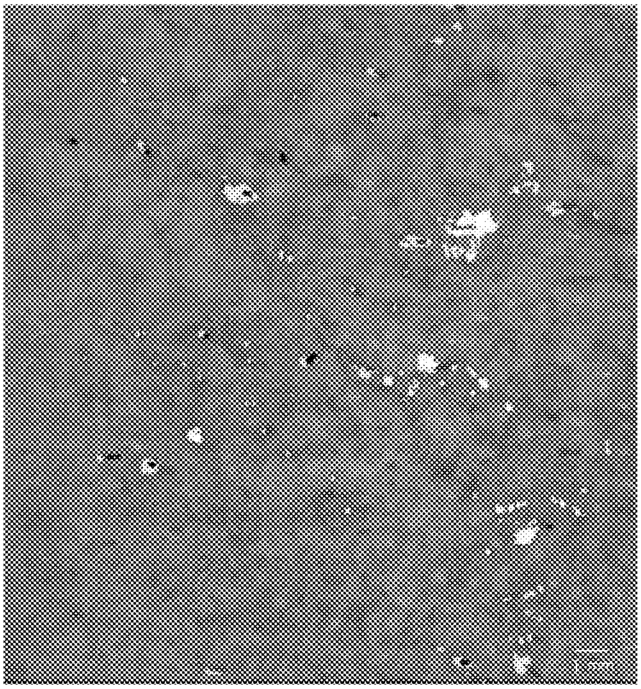
FIG. 17B depicts vascular lesion and melanin lesion depth map as an output of the current invention.

FIG. 17A is a flow chart depicting a method for generating a combined vascular lesion and skin lesion depth map as seen in FIG. 17B.

At block 1701, the skin diagnostic system is configured to receive image skin data comprising a plurality of monochromatic images of target skin.

At block 1703, the skin diagnostic system is configured to identify, by the vascular depth model one label for each of the plurality of monochromatic images and pixels and the label is one of four classifications. The four classifications are background, vascular lesion deep, vascular lesion medium and vascular lesion shallow.

At block 1705, the skin diagnostic system is configured to receive, by the pigment depth model, image skin data comprising two monochromatic images of target skin.

At block 1707, the skin diagnostic system is configured to also receive, by the pigment depth model, output of the vascular depth model of the classifications for vascular lesions regardless of depth. The pigment depth model does not analyze the pixels already labeled vascular lesions.

At block 1709, the system is configured to determine, by the pigment depth model, outliers in darkness of the two wavelength values.

At block 1711, the system is configured to label, by the pigment depth model, the low wavelength value outliers as shallow pigment lesions per pixel and the high wavelength value as deep pigment lesions per pixel.

At block 1713, the system is configured to generate a display utilizing each pixel of one image labeled in 1 of 6 classifications determined. The classifications are background, deep pigment lesion, shallow pigment lesion, deep vascular lesion, medium vascular lesion, and shallow vascular lesion.

In some embodiments, a vascular lesion value and a pigment lesion value are calculated and displayed for the medical personnel. For vascular, the vascular lesion regions relative to total image pixels. For example, Vascular Value=the vascular lesion regions relative to total image pixels. For example, Vascular Value=Total Pixels in Vascular Lesion Map/Total Pixels in image Displayed Units: % of image area (0-100%). For pigment, the pigment lesion regions relative to total image pixels. For example, Pigment Lesion Value=Total Pixels in Pigment Lesion Map/Total Pixels in image Displayed Units: % of image area (0-100%).

In some embodiments, the skin diagnostic system will calculate and generate a ratio, displayed in units of percentage, of a vascular lesion to pigment lesions for the medical personnel. This may aid a medical professional determining which to treat first. By way of specific example, Ratio of Vascular to Pigment Lesions=Total Pixels (or mm) in Vascular Lesion Map/Total Pixels (or mm) image in Pigment Lesion Map.

Pigment Intensity

In some embodiments, pigment intensity of a pigment lesion is automatically determined by a pigment intensity module in the one or more modules 107. Typically, pigment intensity is the contrast between a pigment lesion and the background skin of target skin tissue. This contrast of the lesion to the surrounding target skin is typically determined by a medical professional thus a human eye. Therefore, the contrast is determined not only on the empirical difference between a pigment lesion intensity and surrounding target skin Intensity, but also a human impression non-linear of baseline (dark or light background) of the surrounding skin. The intensity of a pigment lesion (contrast of pigment lesion to surrounding skin) may be used as a treatment input for calculating amount of energy needed to treat the pigment lesion.

In some embodiments, the pigment intensity module comprises a machine learning random forest classification model having two outputs light or dark lesion, hereinafter the pigment intensity model. Typically, the intensity, or contrast of brightness is nonlinear and depends on baseline intensity of skin. In some embodiments, the pigment intensity model is trained with images of target skin labeled with the intensity of the lesion.

In some embodiments, pigment intensity model receives data of three features from each of a plurality of monochromatic images. Feature 1 is a threshold of the 99-percentile of concentration of melanin representing the lesion. Feature 2 is a calculated median melanin level of the whole image, that is an output from the melanin density module that uses the LUT. Finally, feature 3 comprises feature 1 subtracted from feature 2. The output of the image intensity model is either a light or dark lesion. In some embodiments, the pigment intensity data is collected in the memory for further development of pigment Intensity models.

Hair Attributes

In some embodiments, hair attributes in target skin are automatically determined by a hair attributes module of the one or more modules 107. In some embodiments, the hair attributes module receives the output of the hair mask model to identify the hair in the target skin. In some embodiments, the hair attributes module comprises a machine or deep learning classifier model (hereinafter hair attributes model) trained with labeled skin images of medical personnel to detect hair color and hair texture.

In some embodiments, the hair attributes model is trained to determine the color of the hair with labeled target skin images by pixel labeling the hair to a color. After subjective training with the labeled skin images, the classifier will generate the number of classifications for the hair color. In some embodiments, the hair color is four classifications of: blond/red, light brown, dark brown, and black.

In some embodiments, the hair attributes model is trained to determine the hair texture. In some embodiments, the input data for determining hair texture is one monochromatic image of the target skin images. The one image may be a wavelength between about 590 nm to about 720 nm. Each image is a known size and therefore a counting of the pixels of each hair, specifically the pixels of the width of the hair, may determine a hair diameter for each hair. Likewise, counting the pixels of hair compared to overall pixels may determine hair density. The information on hair density and hair diameters, along with subjective labeled training of a machine learning classifier may generate classifications for the hair texture. In an alternative method, a threshold of diameters for each classification may be determined for classification. In some embodiments, the hair texture is three classifications of: fine, medium and course. In some embodiments, the hair attributes model also determine hair thickness, hair melanin level, and hair count.

Treatment Based on Models

In some embodiments, the skin diagnostic system generates the skin attributes and maps discussed above as input to skin treatment modules of the one or more treatment modules 109 to generate parameters to treat target skin. In some embodiments, the skin treatment module comprises a machine or deep learning model (hereinafter skin treatment model). Treatment parameters may include peak energy, energy fluence, pulse width, temporal profile, spot size, wavelength, train of pulses, and others. In some embodiments, the skin diagnostic system skin attributes and maps data may be collected and stored in memory for further development and training of diagnostic and skin treatment models.

Among the skin lesions or problems (hereinafter skin problem indications) to be treated include, but are not limited to: vascular lesions, pigment lesions, melasma, telangiectasia, poikiloderma, age spots, acne facial, acne non-facial and hair removal. The vascular lesions and pigment lesions that may be treated may include but are not limited to; port wine stains hemangioma, leg veins, rosacea, erythema of rosacea, lentigines, keratosis (growth of keratin on the skin), café-au-lait, hemosiderin, becker nevus (a non-cancerous, large, brown birthmark), nevus of ota/ito (ocular dermal melanosis), acne, melasma and hyperpigmentation. Some skin conditions are a combination of pigment and vascular lesions such as, but not limited to; poikiloderma, age spots, and telangiectasia.

Figure 18:
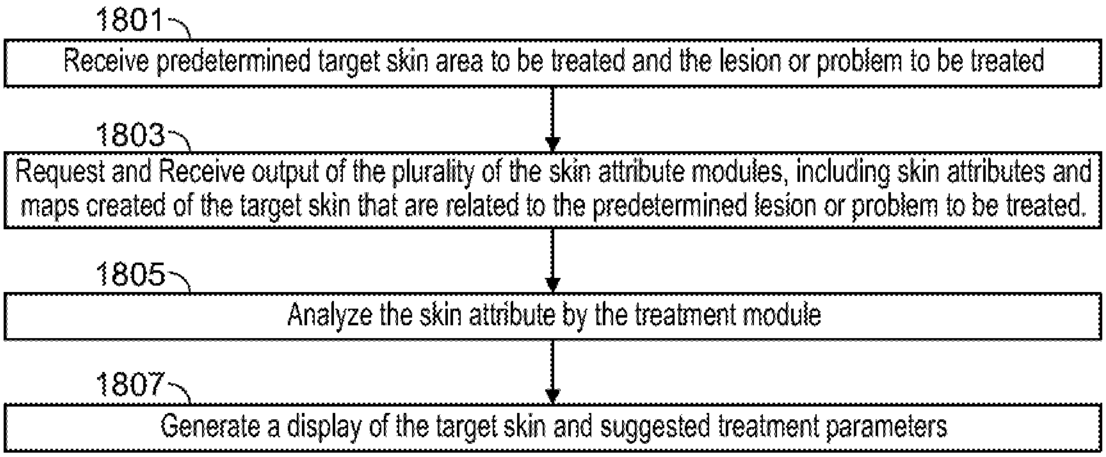
FIG. 18 is a flow chart depicting a method for generating a recommendation of treatment parameters of the current invention.

FIG. 18 is a flow chart depicting a method for generating suggested treatment parameters.

At block 1801, the skin treatment model of the skin diagnostic system is configured to receive predetermined target skin area to be treated and the skin problem indication to be treated from the medical personnel and/or a user of the system. In some embodiments, the treatment skin model also receives treatment safety parameters and parameters of the ability of the energy treatment source. The user of the system may choose a plurality of skin area where target akin is, as well as a plurality of skin problem indications to be treated for each skin area. The user of the system may be instructed on a display to guide the user as to where to aim the skin imaging handpiece 1300 to collect the image skin data required for the plurality of skin attribute models.

At block 1803, the skin treatment model of the skin diagnostic system is configured to receive output of the plurality of the skin attribute models of the target skin that are related to the predetermined skin problem indications to be treated.

In some embodiments, when the treatment is for a vascular lesion, the input to the skin treatment model is the skin type and the vascular lesion depths. In some embodiments, when the treatment is for a pigment lesion, the input to the skin treatment model is the skin type, the pigment lesion depths, and pigment intensity which employs the melanin density to determine pigment intensity. In some embodiments, when the treatment is for combined pigment and vascular lesions, the input to the skin treatment model is the skin type, the vascular lesion depths, the pigment lesion depths, and pigment intensity which employs the melanin density to determine pigment. In some embodiments when the treatment is for hair removal, the input to the skin treatment model is skin type, hair color, and hair texture.

At block 1805, the skin treatment model of the skin diagnostic system is configured to analyze the skin attribute (s) for the predetermined skin treatment. In some embodiments, a plurality of skin treatment lookup tables, one for each of the skin problem indications to be treated, is employed by the skin treatment model to match the skin attributes with the appropriate skin treatment parameters. In some embodiments, the treatment lookup tables are developed specifically for IPL energy-based treatment. The plurality of skin treatment lookup tables may be generated by medical personnel input and an huge set of data collected by clinical trials.

At block 1807, the skin diagnostic system is configured to determine and generate a display of suggested treatment parameters. In some skin diagnostic systems, the system is configured to display an RGB image of the target skin with the suggested treatment parameters. In some embodiments, a plurality of maps of the target skin related to the treatment are displayed, such as but not limited to, a melanin density map, a vascular density map, a pigment lesion depth map, a vascular lesion depth map, a pigment intensity or any combination thereof. These maps may aid the medical personnel and/or the user to change what treatment parameters to use. In some embodiments, reports of the treatment recommended, the treatment done, a plurality of maps of the target skin are all saved in a database for future training of machine learning models, for future display to the user and for future generating of a report per a patient.

In some embodiments, the skin diagnostic system 100 or the combined system 100A may include a diagnose module with a deep or machine learning model to diagnose the skin problem indications to be treated using the image skin data without medical personnel or user input required. In some embodiments, the combined system 100A also has a treatment determination module with a deep learning or a machine learning model to analyze and determine the treatment of the target skin based on the image skin data.

In some embodiments, the training of a diagnose module and/or the treatment determination module are trained with images that may use additional skin attributes data not historically considered to determine treatment. In some embodiments, the system may capture an image of a target skin area and based on the image and deep and/or machine learning determine both a treatment and output a simulation image of the target skin area after treatment.

In some embodiments, the treatment source is an intense pulse light (IPL) treatment source. In some embodiments, the IPL treatment source uses different filters for treatment and by way of specific example a special filter for acne.

In some embodiments, the treatment source has both an image capture device and treatment sourced in the same handpiece. In these cases, the handpiece may be operable in two modes: a treatment mode for delivery of energy-based treatment from, e.g. an intense pulsed light (IPL) source, to an area of a patient's skin; and a diagnostic mode for acquiring an image of the area of skin. In some embodiments, the apparatus is a handpiece of a therapeutic IPL source system, by a tethered connection to the system.

The switching of the system between the two modes may be made in a relatively short time (at most a few seconds, in some embodiments), such that in-treatment monitoring is achievable. Furthermore, in some embodiments, the apparatus sends image data to a akin diagnostic system, which analyzes images and computes an optimal treatment parameter, at least the optimal parameters for the next delivery, and sends the optimal treatment course to the controller or a display of the apparatus in real time. The apparatus enables, for example, iterations of imaging the skin after a delivery of energy-based treatment and deciding parameters of the next delivery without undue delay. "In-treatment" monitoring does not imply that monitoring is necessarily taking place at the same time as treatment. The system may switch between the treatment mode and the diagnostic mode within a period of time sufficiently short to the user, i.e. several seconds. During a treatment the system may switch between treatment and diagnostic modes multiple times. Details on a skin treatment and real time monitoring with combined treatment and image capturing handpiece is further described in PCT Serial No. PCT/IL2023/050785 filed 30 Jul. 2023 which is hereby incorporated by reference in its entirety.

Throughout the specification, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments may be readily combined, without departing from the scope or spirit of the present disclosure.

The terms "a", "an" and "the" mean "one or more", unless expressly specified otherwise.

Throughout the specification, the word "exemplary" is used herein to mean "serving as an example, instance, or illustration." Any embodiment or implementation of the present subject matter described herein as "exemplary" is not necessarily to be construed as preferred or advantageous over other embodiments.

The terms "comprises", "comprising", or any other variations thereof, are intended to cover a non-exclusive inclusion, such that a setup, device, or method that comprises a list of components or steps does not include only those components or steps but may include other components or steps not expressly listed or inherent to such setup or device or method. In other words, one or more elements in a system or apparatus proceeded by "comprises . . . a" does not, without more constraints, preclude the existence of other elements or additional elements in the system or method.

The terms "includes", "including", or any other variations thereof, are intended to cover a non-exclusive inclusion, such that a setup, device, or method that includes a list of components or steps does not include only those components or steps but may include other components or steps not expressly listed or inherent to such setup or device or method. In other words, one or more elements in a system or apparatus proceeded by "includes . . . a" does not, without more constraints, preclude the existence of other elements or additional elements in the system or method.

In addition, the term "based on" is not exclusive and allows for being based on additional factors not described, unless the context clearly dictates otherwise. In addition, throughout the specification, the meaning of "a," "an," and "the" include plural references. The meaning of "in" includes "in" and "on."

It is understood that at least one aspect/functionality of various embodiments described herein can be performed in real-time and/or dynamically. As used herein, the term "real-time" or "near real-time" is directed to an event/action that can occur instantaneously or almost instantaneously in time when another event/action has occurred. For example, the "real-time processing," "real-time computation," and "real-time execution" all pertain to the performance of a computation during the actual time that the related physical process (e.g., a user interacting with an application on a mobile device) occurs, in order that results of the computation can be used in guiding the physical process. In some embodiments, events and/or actions in accordance with the present disclosure can be in real-time, near real-time, and/or based on a predetermined periodicity of at least one of: nanosecond, several nanoseconds, millisecond, several milliseconds, second, several seconds, minute, several minutes, hourly, several hours, daily, several days, weekly, monthly, etc. As used herein, the term "dynamically" and term "automatically," and their logical and/or linguistic relatives and/or derivatives, mean that certain events and/or actions can be triggered and/or occur without any human intervention.

Computer systems, and systems, as used herein, can include any combination of hardware and software. Examples of software may include software components, programs, applications, operating system software, firmware, software modules, routines, subroutines, functions, methods, procedures, software Interfaces, Application Programming Interfaces (API), computer code, data, data variables, or any combination thereof that can be processed by a computing device as computer-executable instructions.

In some embodiments, one or more of computer-based systems of the present disclosure may include or be incorporated, partially or entirely into at least one Personal Computer (PC), laptop computer, tablet, portable computer, smart device (e.g., smart phone, smart tablet or smart television), Mobile Internet Device (MID), messaging device, data communication device, server computer, and so forth.

The illustrated of method FIG. 7 shows certain events occurring in a certain order. In alternative embodiments, certain operations may be performed in a different order, modified, or removed. Moreover, steps may be added to the above-described logic and still conform to the described embodiments. Further, operations described herein may occur sequentially or certain operations may be processed in parallel. Yet further, operations may be performed by a single processing unit or by distributed processing units.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based here on. Accordingly, the disclosure of the embodiments of the invention is intended to be illustrative, but not limiting, of the scope of the invention, which is set forth in the following claims.

The invention claimed is:

1. A system for determining skin attributes and treatment parameters of target skin for an aesthetic skin diagnosis and treatment unit, comprises:
- a display;
- at least one source for illumination light;
- an image capture device;
- an energy source for providing energy-based treatment;
- a processor;
- a memory communicatively coupled to the processor, wherein the memory stores processor-executable instructions, which, on execution, cause the processor to:
  - activate the at least one source for illumination light to illuminate in a plurality of monochromatic wavelengths;
  - obtain images from the image capture device in the plurality of monochromatic wavelengths;
  - receive target skin data comprising data of each pixel of the obtained images;
  - analyze the target skin data using a plurality of trained skin attribute models;
  - determine, with the trained skin attribute models, at least one skin attributes classification of the target skin;
  - analyze, with a trained skin treatment model, the at least one classification for the skin attributes of the target skin;
  - identify, with the trained skin treatment model, treatment parameters for the energy source of energy-based treatment for the at least one skin attributes classification determined;
  - display the treatment parameters identified to treat the skin attributes; and
  - activate the energy source for providing energy-based treatment to treat the target skin with the treatment parameters determined, wherein the at least one skin attributes is at least one of melanin density, vascular density and scattering; and the processor is further configured to:
- receive skin type data comprising a plurality of absolute reflectance values for each pixel representing the plurality of wavelengths;
- analyze the plurality of absolute values per pixel, with at least one of a melanin model or a vascular model, compared with a look up table (LUT) values, wherein the LUT comprises value for skin models that represent known physical models of illumination effects on human skin and represent physical measurements of concentration of the skin attributes in the target skin;
- identity for each pixel the one LUT entry for at least one of melanin density or vascular density with the value closest in distance to the plurality of measured absolute values for each pixel, wherein this distance may be a similarity of certain distances
- receive a value in the LUT of at least one of the melanin density from the melanin model or the vascular density form the vascular model;
- compute a new value for the melanin density or the vascular density based on setting other skin attributes on the LUT closest to zero; and
- generate a map of the target skin for either the melanin density or the vascular density using the new value wavelengths computed.

2. The system of claim 1, wherein the system generates and displays a list of attributes of the target skin based on the analysis by the trained skin attribute models.

3. The system of claim 1, wherein the plurality of trained skin attribute models are trained by;
- (i) providing a plurality of labelled images of at least one skin attribute stored in a database to the skin attribute models, and
- (ii) configuring the skin attribute models to classify the plurality of labelled images into at least one skin attribute.

4. The system of claim 1, wherein the plurality of different wavelengths comprises 450 nm, 490 nm, 570 nm, 590 nm, 660 nm, 770 nm, and 850 nm.

5. The system of claim 1, wherein the processor is further configured, after obtaining the images, to register and align the images of the plurality of monochromatic wavelengths.

6. The system of claim 1, wherein the processor is further configured to generate and display said map of the target skin from the wavelengths that represent red, green, and blue.

7. The system of claim 1, wherein one of the skin attributes is hair on the target skin and a hair mask model is one of the plurality of skin attribute models and the processor is further configured to:

receive the target skin data of one monochromatic wavelengths of the plurality of monochromatic wavelengths; and determine, with the hair mask model, one of two classifications, hair or background, for each pixel of an image of the one monochromatic wavelength.

8. The system of claim 7, wherein the processor is further configured to:

instruct additional skin attribute models to remove hair pixels labeled hair by the hair mask model from further analysis of target skin.

9. The system of claim 1, wherein one of the skin attributes is skin type and a skin type model is one of the plurality of skin attribute models.

10. The system of claim 9, wherein the processor is further configured to:

receive skin type data comprising an average calibrated reflectance value of total pixels of each monochrome image; and determine with the skin type model, six classifications of skin type.

11. The system of claim 1, wherein one of the skin attributes is vascular lesion depth and a vascular depth model is one of the plurality of skin attribute models.

12. The system of claim 11, wherein the processor is further configured to:

receive the target skin data of the plurality of monochromatic wavelengths; and determine a classification for each pixel, with a vascular lesion model, of one of four classifications, deep vascular, medium vascular, shallow vascular or background; and generate and display a map with markings to illustrate the classifications of vascular lesion depths.

13. The system of claim 1, wherein the processor with the trained skin treatment model, are further configured to:

receive information of;

treatment safety parameters, energy treatment source capability parameters, at least one skin area to treat from a user, at least one skin problem indication for treatment based on the skin area to treat from a user, output of the plurality of the skin attribute models related to the at least one skin problem indication;

determine, based on the information received, target skin treatment parameters of the energy-based treatment; and display the target skin treatment parameters of the energy-based treatment.

14. The system of claim 13, wherein the determination of the skin treatment parameters is done with a treatment lookup table and the processor is further configured to:

determine which one of a plurality of skin treatment look up tables, each of the skin treatment look up tables is based on a particular skin problem indication;

match the output of the plurality of the skin attribute models to a treatment parameter of the determined skin treatment look up table; and display the matched skin treatment parameters of the energy-based treatment.

15. The system of claim 13, wherein the processor with the trained skin treatment model, are further configured to:

generate and display a red green and blue (RGB) image of the target skin;

generate and save to memory at least one of a plurality of maps, display the at least one generated map, wherein the at least one of the plurality of maps further comprises;

pigment lesion depth map, vascular lesion depth map, pigment intensity, or any combination thereof.

16. The system of claim 13, wherein the at least one skin problem indication is at least one of;

pigment lesions, vascular lesions, combination pigment and vascular lesion, hair removal, or any combination thereof.

17. A system for determining skin attributes and treatment parameters of target skin for an aesthetic skin diagnosis and treatment unit, comprises:

a display;

at least one source for illumination light;

an image capture device;

an energy source for providing energy-based treatment;

a processor;

a memory communicatively coupled to the processor, wherein the memory stores processor-executable instructions, which, on execution, cause the processor to:

activate the at least one source for illumination light to illuminate in a plurality of monochromatic wavelengths;

obtain images from the image capture device in the plurality of monochromatic wavelengths;

receive target skin data comprising data of each pixel of the obtained images;

analyze the target skin data using a plurality of trained skin attribute models;

determine, with the trained skin attribute models, at least one skin attributes classification of the target skin;

analyze, with a trained skin treatment model, the at least one classification for the skin attributes of the target skin;

identify, with the trained skin treatment model, treatment parameters for the energy source of energy-based treatment for the at least one skin attributes classification determined;

display the treatment parameters identified to treat the skin attributes; and activate the energy source for providing energy-based treatment to treat the target skin with the treatment parameters determined, wherein one of the skin attributes is pigment lesion depth and a pigment depth model is one of the plurality of skin attribute models; and the processor is further configured to:

receive the target skin data of two monochromatic wavelengths of the plurality of monochromatic wavelengths, wherein one of the two monochromatic wavelengths represents a lowest wavelength value of the system, and a second one of the two monochromatic wavelengths represents a highest wavelength value of the system;

receive, from a vascular depth model, classified pixels of vascular depth;

analyze pixels not classified by the vascular depth model, for outliers in darkness for each of the two monochromatic wavelengths;

determine a classification for each pixel analyzed, with the pigment depth model, the outliers of the lowest wavelength value as shallow pigment lesions and the highest wavelength value as deep pigment lesions; and generate and display a map with markings to illustrate classifications of the pigment lesion depths.

18. A system for determining skin attributes and treatment parameters of target skin for an aesthetic skin diagnosis and treatment unit, comprises:

a display;

at least one source for illumination light;

an image capture device;

an energy source for providing energy-based treatment;

a processor;

a memory communicatively coupled to the processor, wherein the memory stores processor-executable instructions, which, on execution, cause the processor to:

activate the at least one source for illumination light to illuminate in a plurality of monochromatic wavelengths;

obtain images from the image capture device in the plurality of monochromatic wavelengths;

receive target skin data comprising data of each pixel of the obtained images;

analyze the target skin data using a plurality of trained skin attribute models;

determine, with the trained skin attribute models, at least one skin attributes classification of the target skin;

analyze, with a trained skin treatment model, the at least one classification for the skin attributes of the target skin;

identify, with the trained skin treatment model, treatment parameters for the energy source of energy-based treatment for the at least one skin attributes classification determined;

display the treatment parameters identified to treat the skin attributes; and activate the energy source for providing energy-based treatment to treat the target skin with the treatment parameters determined, wherein one of the skin attributes is pigment lesion depth and a pigment depth model is one of the plurality of skin attribute models; and the processor is further configured to:

receive the target skin data of three features from each of the plurality of monochromatic images, wherein the features are a threshold of a 99-percentile of concentration of melanin representing the lesion, a calculated median melanin level of the whole image from a melanin density model and the 99-percentile subtracted from the calculated median melanin level; and determine, based on the features, if the pigment lesion intensity is either a light or dark lesion.

19. A method for determining skin attributes and treatment parameters of target skin comprises:

providing a display, at least one source for illumination light, an image capture device, an energy source for providing energy-based treatment, a memory and processor;

activating, by the processor, the at least one source for illumination light to illuminate in a plurality of monochromatic wavelengths;

obtaining, by the processor, images from the image capture device in the plurality of monochromatic wavelengths;

receiving, by the processor, target skin data comprising data of each pixel of the obtained images;

analyzing, by the processor, the target skin data using a plurality of trained skin attribute models;

determining, by the processor with the trained skin attribute models, at least one skin attributes classification of the target skin;

analyzing, by the processor with a trained skin treatment model, the at least one classification for the skin attributes of the target skin;

identifying, by the processor with the trained skin treatment model, treatment parameters for the energy source for energy-based treatment for the at least one skin attributes classification determined;

displaying, by the processor, the treatment parameters identified to treat the skin attributes; and activating the energy source for providing energy-based treatment to treat the target skin with the treatment parameters determined, wherein the skin attribute is at least one of melanin density, vascular density and scattering; and wherein the method further comprises:

receiving, by the processor, skin type data comprising a plurality of absolute reflectance values for each pixel representing the plurality of wavelengths;

analyzing, by the processor, the plurality of absolute values per pixel, with at least one of a melanin model or a vascular model, compared with a look up table (LUT) values, wherein the LUT comprises values for skin models that represent known physical models of illumination effects on human skin and represent physical measurements of concentration of the skin attributes in the target skin;

identifying, by the processor, for each pixel the one LUT entry for at least one of melanin density or vascular density with the value closest in distance to the plurality of measured absolute values for each pixel, wherein this distance may be a similarity of certain distances;

receiving, by the processor, the value in the LUT of at least one of, the melanin density value from the melanin model or the vascular density value from the vascular model;

computing, by the processor, a new value for the melanin density value or the vascular density value based on setting other skin attributes on the LUT closest to zero; and generating, by the processor, a map of either the melanin density or the vascular density using the new value wavelengths computed.

20. The method of claim 19, wherein the method further comprises:

receiving, by the processor with the trained skin treatment model information of;

treatment safety parameters, energy treatment source capability parameters, at least one skin area to treat from a user, at least one skin problem indication for treatment based on the skin area to treat from a user, output of the plurality of the skin attribute models related to the at least one skin problem indication;

determining, by the processor with the trained skin treatment model, based on the information received, target skin treatment parameters of the energy-based treatment; and displaying, by the processor with the trained skin treatment model, the target skin treatment parameters of the energy-based treatment.

21. The method of claim 20, wherein the determining of the skin treatment parameters is done with a treatment look up table and the method further comprise:

determining, by the processor with the trained skin treatment model, which one of a plurality of skin treatment look up tables, wherein each of the skin treatment look up tables is based on a particular skin problem indication;

matching, by the processor with the trained skin treatment model, the output of the plurality of the skin attribute models to a treatment parameter of the determined skin treatment look up table; and displaying, by the processor, the matched skin treatment parameters of the energy-based treatment.

* * * * *